(12) United States Patent
Malcolm et al.

(10) Patent No.: US 9,427,400 B2
(45) Date of Patent: *Aug. 30, 2016

(54) PLATINUM-CATALYZED INTRAVAGINAL RINGS

(71) Applicant: International Partnership for Microbicides, Silver Spring, MD (US)

(72) Inventors: Karl Malcolm, Belfast (IE); David Woolfson, Belfast (IE); Joseph Romano, Wayne, PA (US)

(73) Assignee: International Partnership For Microbicides, Silver Spring, MD (US)

( * ) Notice: Subject to any disclaimer, the term of this patent is extended or adjusted under 35 U.S.C. 154(b) by 8 days.

This patent is subject to a terminal disclaimer.

(21) Appl. No.: 14/051,544

(22) Filed: Oct. 11, 2013

(65) Prior Publication Data
US 2014/0056961 A1    Feb. 27, 2014

(51) Int. Cl.
    *A61K 9/00*      (2006.01)
    *A61K 31/505*    (2006.01)
    *A61K 31/444*    (2006.01)

(52) U.S. Cl.
CPC ........... *A61K 9/0036* (2013.01); *A61K 31/444* (2013.01); *A61K 31/505* (2013.01)

(58) Field of Classification Search
CPC ............. A61K 9/0036; A61K 31/505; A61K 31/551; A61K 31/496; A61K 31/535
See application file for complete search history.

(56) References Cited

U.S. PATENT DOCUMENTS

| | | |
|---|---|---|
| 3,545,439 A | 12/1970 | Kalamazoo et al. |
| 3,710,795 A | 1/1973 | Higuchi et al. |
| 3,832,252 A | 8/1974 | Higuchi et al. |
| 3,854,480 A | 12/1974 | Zaffaroni |
| 3,916,899 A | 11/1975 | Theeuwes et al. |
| 3,920,805 A | 11/1975 | Roseman |
| 3,948,254 A | 4/1976 | Zaffaroni |
| 3,991,760 A | 11/1976 | Drobish et al. |
| 3,995,633 A | 12/1976 | Gougeon |
| 4,012,496 A | 3/1977 | Schopflin et al. |
| 4,012,497 A | 3/1977 | Schopflin |
| 4,014,987 A | 3/1977 | Heller et al. |
| 4,016,251 A | 4/1977 | Higuchi et al. |
| 4,043,339 A | 8/1977 | Roseman |
| 4,093,709 A | 6/1978 | Choi et al. |
| 4,155,991 A | 5/1979 | Schopflin et al. |
| 4,202,880 A | 5/1980 | Fildes et al. |
| 4,235,236 A | 11/1980 | Theeuwes |
| 4,237,885 A | 12/1980 | Wong et al. |
| 4,237,888 A | 12/1980 | Roseman et al. |
| 4,250,611 A | 2/1981 | Wong |
| 4,286,587 A | 9/1981 | Wong |
| 4,292,965 A | 10/1981 | Nash et al. |
| 4,469,671 A | 9/1984 | Zimmerman et al. |
| 4,493,699 A | 1/1985 | Zimmerman et al. |
| 4,553,972 A | 11/1985 | Vickery |
| 4,564,362 A | 1/1986 | Burnhill |
| 4,589,880 A | 5/1986 | Dunn et al. |
| 4,596,576 A | 6/1986 | de Nijs |
| 4,762,717 A | 8/1988 | Crowley, Jr. |
| 4,822,616 A | 4/1989 | Zimmermann et al. |
| 4,888,074 A | 12/1989 | Pocknell |
| 4,997,653 A | 3/1991 | Igarashi |
| 5,398,698 A | 3/1995 | Hiller et al. |
| 5,660,187 A | 8/1997 | Hiller et al. |
| 5,694,947 A | 12/1997 | Lehtinen et al. |
| 5,788,980 A | 8/1998 | Nabahi |
| 5,855,906 A | 1/1999 | McClay |
| 5,869,081 A | 2/1999 | Jackanicz et al. |
| 5,972,372 A | 10/1999 | Saleh et al. |
| 5,989,581 A | 11/1999 | Groenewegen |
| 6,039,968 A | 3/2000 | Nabahi |

(Continued)

FOREIGN PATENT DOCUMENTS

| | | |
|---|---|---|
| EP | 81370 A1 | 6/1983 |
| EP | 1732520 B1 | 6/2009 |

(Continued)

OTHER PUBLICATIONS

Ampofo et al., Comparative Study of Dissolution Profiles of Microbicide Ring Products Prepared from Different Silicone Elastomer Sources, Poster Presented at AAPS, Los Angeles, CA, USA, Nov. 9, 2009.
Bell et al., Characterization of silicon elastomer vaginal rings containing HIV microbicide TMC120 by Raman spectroscopy, J. Pharmacy and PHarmacol., 59:203-207, 2007.
Edwards et al., Evaluation of content uniformity using a 3-stream versus 2-stream mixing process to manufacture silicone based vaginal rings, Poster Presented at AAPS, Los Angeles, CA, USA, Nov. 9, 2009.
Gupta et al., Polyurethane Intravaginal ring for controlled delivery of dapivirine, a nonnucleoside reverse transcriptase inhibitor of HIV-1, J. Pharmaceutical Sci., 97(10):4228-4239, 2008.
Howard-Sparks et al., Release characteristics of dapivirine and tenofovir from vaginal rings consisting of ethylene vinyl acetate, silicone or polyurethane polymers: options for HIV prevention, Poster Presented at AAPS, Los Angeles, CA, USA, Nov. 8-12, 2009.
Malcolm et al., Long-term, controlled release of the HIV microbicide TMC120 from silicone elastomer vaginal rings, J. Antimicrobial Chemotherapy, 56:954-956, 2005.

(Continued)

*Primary Examiner* — Jessica Worsham
(74) *Attorney, Agent, or Firm* — McCarter & English, LLP; Maria Laccotripe Zacharakis; Marcie B. Clarke

(57) ABSTRACT

The present invention provides improved intravaginal drug delivery devices, i.e., intravaginal rings, useful for the prophylactic administration of an antimicrobial compound, e.g., Dapivirine, to a human. The intravaginal rings of the invention address previous stability issues by utilizing a platinum catalyst (e.g., in the form of a platinum-siloxane complex) for the cross-linking reaction. The vaginal rings surprisingly achieve relatively high and steady release rates in vivo with a matrix ring containing a relatively small loading dose. While the matrix rings of the present invention have in vivo the steady release rates associated with reservoir rings, they are easier and less expensive to manufacture. The present invention also provides methods of blocking DNA polymerization by an HIV reverse transcriptase enzyme, methods of preventing HIV infection in a female human, methods of treating HIV infection in a female human, and methods of preparing platinum-catalyzed intravaginal rings.

42 Claims, 9 Drawing Sheets

(56) References Cited

U.S. PATENT DOCUMENTS

| | | |
|---|---|---|
| 6,063,325 A | 5/2000 | Nahill et al. |
| 6,086,909 A | 7/2000 | Harrison et al. |
| 6,103,256 A | 8/2000 | Nabahi |
| 6,126,958 A | 10/2000 | Saleh et al. |
| 6,264,973 B1 | 7/2001 | Mahashabde et al. |
| 6,394,094 B1 | 5/2002 | McKenna et al. |
| 6,566,095 B1 | 5/2003 | Markham et al. |
| 6,740,333 B2 | 5/2004 | Beckett et al. |
| 6,951,654 B2 | 10/2005 | Malcolm et al. |
| 7,001,912 B2 | 2/2006 | Kuki et al. |
| 7,094,909 B2 | 8/2006 | Kucera et al. |
| 7,109,230 B2 | 9/2006 | Erickson et al. |
| 7,138,408 B2 | 11/2006 | Kuki et al. |
| 7,169,932 B2 | 1/2007 | Kucera et al. |
| 7,199,148 B2 | 4/2007 | Tahri et al. |
| 7,521,064 B2 | 4/2009 | Saxena et al. |
| 7,521,074 B2 | 4/2009 | Mikkelsen et al. |
| 7,824,383 B2 | 11/2010 | Sokal et al. |
| 7,829,112 B2 | 11/2010 | Ron et al. |
| 7,833,545 B2 | 11/2010 | Ron et al. |
| 7,838,024 B2 | 11/2010 | Ron et al. |
| 7,850,986 B2 | 12/2010 | Riihimaki |
| 7,883,718 B2 | 2/2011 | Ron et al. |
| 7,910,126 B2 | 3/2011 | Ahmed et al. |
| 7,935,710 B2 | 5/2011 | Van Roey et al. |
| 8,057,817 B2 | 11/2011 | Shalaby |
| 8,062,658 B2 | 11/2011 | Shalaby et al. |
| 8,580,294 B2 | 11/2013 | Malcolm et al. |
| 2002/0161352 A1 | 10/2002 | Lin et al. |
| 2003/0059456 A1 | 3/2003 | Malcolm et al. |
| 2003/0060785 A1 | 3/2003 | Lavean et al. |
| 2003/0134803 A1 | 7/2003 | Cherr et al. |
| 2003/0232088 A1 | 12/2003 | Huang et al. |
| 2004/0089308 A1 | 5/2004 | Welch |
| 2004/0126369 A1 | 7/2004 | Payne et al. |
| 2004/0265355 A1 | 12/2004 | Shalaby |
| 2005/0042292 A1 | 2/2005 | Muldoon et al. |
| 2005/0148995 A1 | 7/2005 | Shepard et al. |
| 2005/0197651 A1 | 9/2005 | Chen et al. |
| 2005/0250746 A1 | 11/2005 | Iammatteo |
| 2006/0083778 A1 | 4/2006 | Allison et al. |
| 2006/0100154 A1 | 5/2006 | Koch et al. |
| 2006/0166943 A1* | 7/2006 | Van Roey et al. ............ 514/150 |
| 2006/0280771 A1 | 12/2006 | Groenewegen et al. |
| 2007/0037780 A1 | 2/2007 | Ebert et al. |
| 2007/0043332 A1 | 2/2007 | Malcolm et al. |
| 2007/0077269 A1 | 4/2007 | Woodward |
| 2007/0196433 A1 | 8/2007 | Ron et al. |
| 2007/0243229 A1 | 10/2007 | Smith et al. |
| 2008/0206310 A1 | 8/2008 | Davis |
| 2008/0268022 A1 | 10/2008 | McCabe et al. |
| 2008/0300197 A1 | 12/2008 | Kabir et al. |
| 2009/0004246 A1 | 1/2009 | Woolfson et al. |
| 2009/0060997 A1 | 3/2009 | Seitz et al. |
| 2009/0081278 A1 | 3/2009 | De Graaff et al. |
| 2009/0142313 A1 | 6/2009 | Talling et al. |
| 2009/0202612 A1 | 8/2009 | Ahmed et al. |
| 2009/0291120 A1 | 11/2009 | Tuominen et al. |
| 2010/0034810 A1 | 2/2010 | Heeres et al. |
| 2010/0034863 A1 | 2/2010 | Fairhurst et al. |
| 2010/0040671 A1 | 2/2010 | Ahmed et al. |
| 2010/0087402 A1 | 4/2010 | Wang et al. |
| 2010/0104619 A1 | 4/2010 | De Graaff et al. |
| 2010/0129425 A1 | 5/2010 | De Graaff et al. |
| 2010/0203104 A1 | 8/2010 | De Graaff et al. |
| 2010/0247564 A1 | 9/2010 | Lee et al. |
| 2010/0285094 A1 | 11/2010 | Gupta |
| 2010/0330138 A1 | 12/2010 | Shalaby et al. |
| 2011/0008409 A1 | 1/2011 | Seitz et al. |
| 2011/0045076 A1 | 2/2011 | Kiser et al. |
| 2011/0165093 A1 | 7/2011 | Van Roey et al. |
| 2011/0189257 A1 | 8/2011 | Chin et al. |
| 2011/0208135 A1 | 8/2011 | Hakala |
| 2011/0236462 A1 | 9/2011 | Shaked et al. |
| 2012/0093911 A1 | 4/2012 | Malcolm et al. |

FOREIGN PATENT DOCUMENTS

| | | |
|---|---|---|
| EP | 2179722 A1 | 4/2010 |
| WO | 9416652 A1 | 8/1994 |
| WO | 9509641 A1 | 4/1995 |
| WO | 9731631 A1 | 9/1997 |
| WO | 9808471 A1 | 3/1998 |
| WO | 9938468 A1 | 8/1999 |
| WO | 99/50250 A1 | 10/1999 |
| WO | 0074684 A1 | 12/2000 |
| WO | 0240021 A2 | 5/2002 |
| WO | 02056793 A2 | 7/2002 |
| WO | 02/076426 A2 | 10/2002 |
| WO | 03061579 A2 | 7/2003 |
| WO | 03077926 A1 | 9/2003 |
| WO | 03089002 A1 | 10/2003 |
| WO | 03/094920 A1 | 11/2003 |
| WO | 2004022033 A1 | 3/2004 |
| WO | 2004030687 A1 | 4/2004 |
| WO | 2004071508 A1 | 8/2004 |
| WO | 2004103159 A2 | 12/2004 |
| WO | 2004103336 A2 | 12/2004 |
| WO | 2005021750 A1 | 3/2005 |
| WO | 2005089723 A1 | 9/2005 |
| WO | 2006010097 A2 | 1/2006 |
| WO | 2006084082 A1 | 8/2006 |
| WO | 2006084083 A2 | 8/2006 |
| WO | 2007012006 A1 | 1/2007 |
| WO | 2007084211 A2 | 7/2007 |
| WO | 2007092326 A2 | 8/2007 |
| WO | 2008007046 A1 | 1/2008 |
| WO | 2008089488 A2 | 7/2008 |
| WO | 2009003125 A1 | 12/2008 |
| WO | 2009021323 A1 | 2/2009 |
| WO | 2009070638 A1 | 6/2009 |
| WO | 2009094190 A2 | 7/2009 |
| WO | 2009111218 A2 | 9/2009 |
| WO | 2009129459 A1 | 10/2009 |
| WO | 2009141309 A1 | 11/2009 |
| WO | 2010054296 A2 | 5/2010 |
| WO | 2010119030 A1 | 10/2010 |
| WO | 2010133652 A1 | 11/2010 |
| WO | 2010133761 A1 | 11/2010 |
| WO | 2011006067 A1 | 1/2011 |
| WO | 2011011099 A1 | 1/2011 |
| WO | 2011011710 A1 | 1/2011 |
| WO | 2011049948 A2 | 4/2011 |
| WO | 2011067302 A1 | 6/2011 |

OTHER PUBLICATIONS

Nel et al., Safety and Pharmacokinetics of Dapivirine Delivery from Matrix and Reservoir Intravaginal Rings to HIV-Negative Women, J. Acquir. Immune Defic. Syndr., 51(4):416-423, 2009.

Romano et al., Safety and Availability of Dapivirine (TMC120) Delivered from an Intravaginal Ring, AIDS Research and Human Retroviruses, 25(5):483-488, 2009.

Woolfson et al., Intravaginal ring delivery of the reverse transcriptase inhibitor TMC.

Cohen et al. (2012) Editorial review "Antiviral agents and HIV prevention: controversies, conflicts and consensus" AIDS p. 1585-1598.

DiFabio et al "Inhibition of vaginal transmission of HIV-1 in hu-SCID mice by the non-nucleotide reverse transcriptase inhibitor TMC120 in a gel formulation" AIDS, vol. 17, No. 11 (2003), p. 1597-1604.

Nel et al (2012) "Safety, Acceptability and Adherence of Monthly Dapivirine Vaginal Microbicide Rings for HIV Prevention" Paper #1089, 19th Conference on Retroviruses and Opportunistic Infections.

* cited by examiner

Figure 3: Formulation Matrix

| FID | API (mg) | Elastomer Base | Stiffness (N) | Filler % |
|---|---|---|---|---|
| 4875 | 25 | Wacker 3003/50 | 0.86 | 20 |
| 4881 | 25 | Dow S70 | 1.83 | 10-30 |
| 4882 | 25 | GE 6071 | 1.59 | 10-30 |
| 4883 | 25 | Nusil MED4870 | 1.68 | 30 |
| 4875 | 0 | Wacker 3003/50 | 1.21 | 20 |
| 4881 | 0 | Dow S70 | 2.27 | 10-30 |
| 4882 | 0 | GE 6071 | 2.91 | 10-30 |
| 4883 | 0 | Nusil MED4870 | 2.25 | 30 |

*Pt-cured silicone elastomer base from each of 4 vendors was blended with dapivirine to produce matrix vaginal rings with 25 mg loading by injection molding. Microscopy results confirmed that dapivirine was uniformly distributed throughout the rings.
FID = formulation identification number

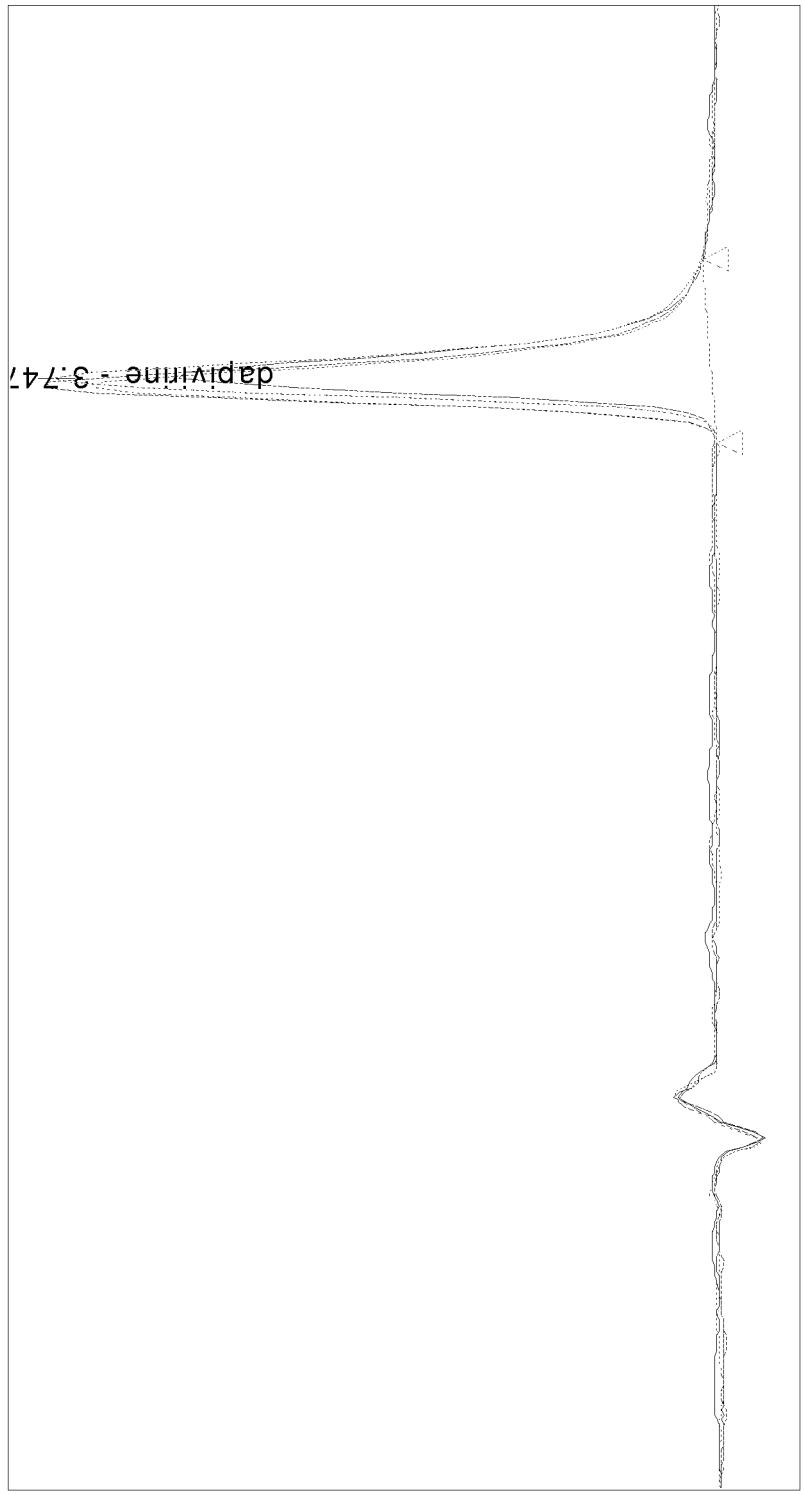
Figure 4: Typical API Chromatogram

Figure 5: Variability in Cumulative API Release (mcg)

| FID | Day 1 | Day 7 | Day 14 | Day 21 | Day 28 |
|---|---|---|---|---|---|
| 4875 | 2271 | 6471 | 9007 | 10879 | 12311 |
| 4881 | 2266 | 6290 | 8573 | 10311 | 11641 |
| 4882 | 2129 | 5549 | 7568 | 10032 | 11429 |
| 4883 | 2222 | 6474 | 9020 | 10859 | 12295 |
| Mean | 2222 | 6196 | 8542 | 10520 | 11919 |
| RSD | 3.0 | 7.1 | 8.0 | 4.0 | 3.8 |

*Day 1 and Cumulative release of API over 28 days was similar for rings produced from 4 different silicone elastomer bases.
FID = formulation identification number

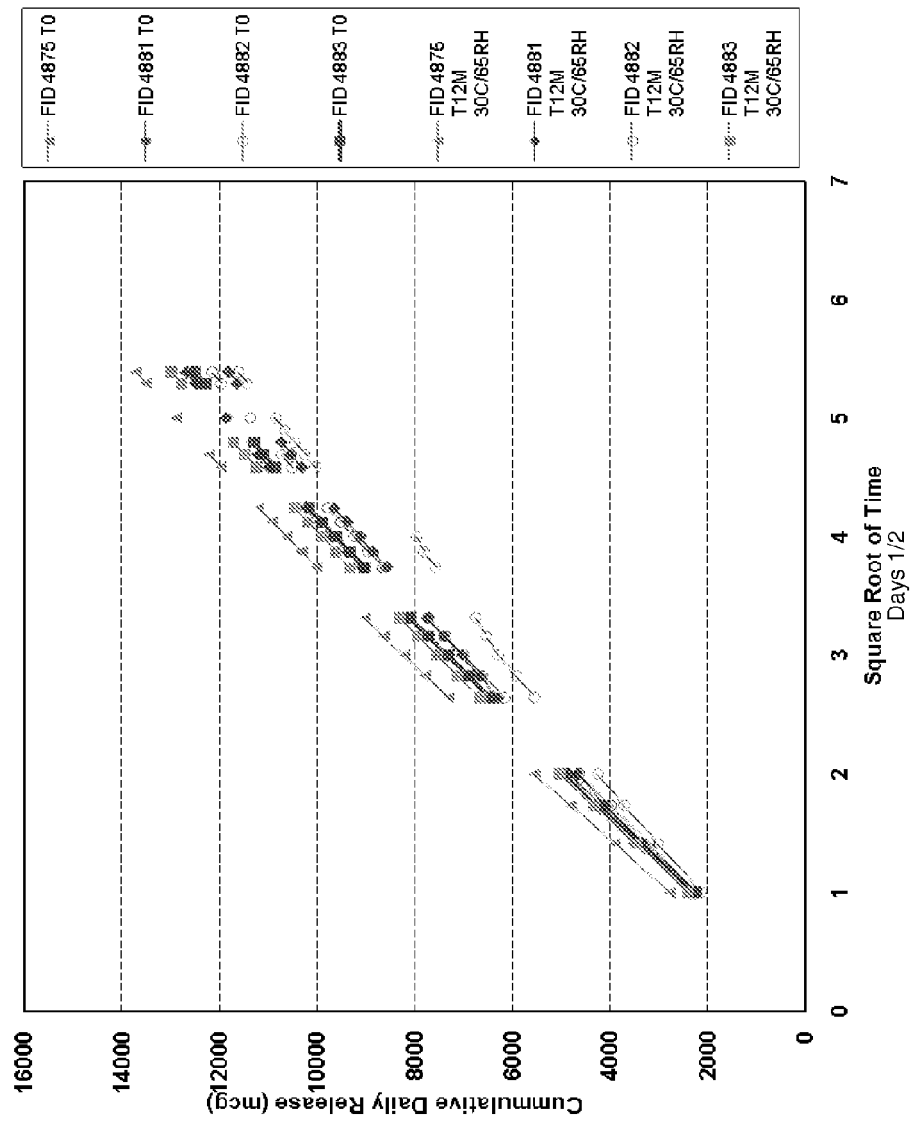
Figure 6: API Cumulative Daily Release as a Function of $t^{1/2}$
*The linearity in the cumulative release over time demonstrates that first order kinetics were followed.

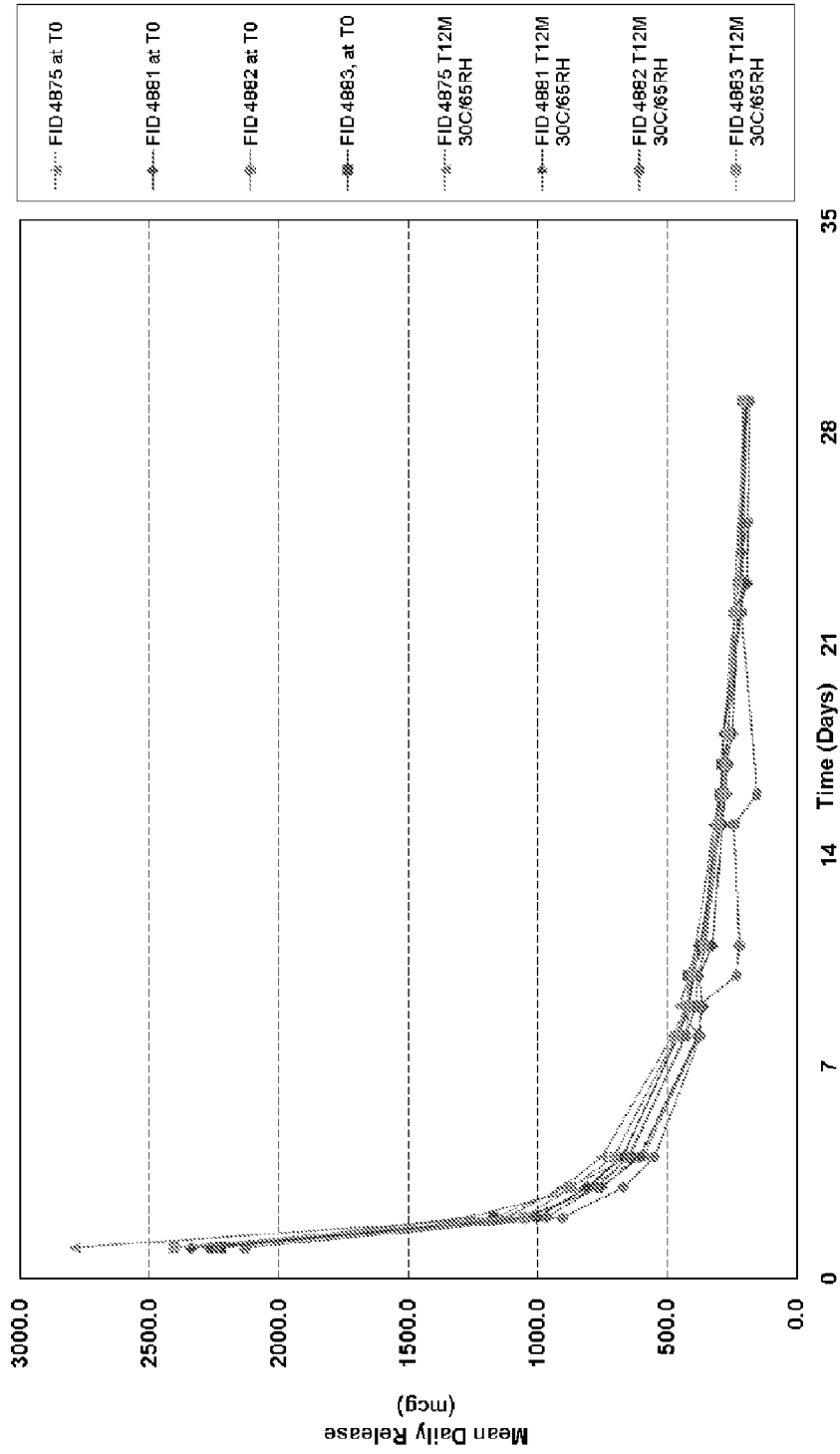

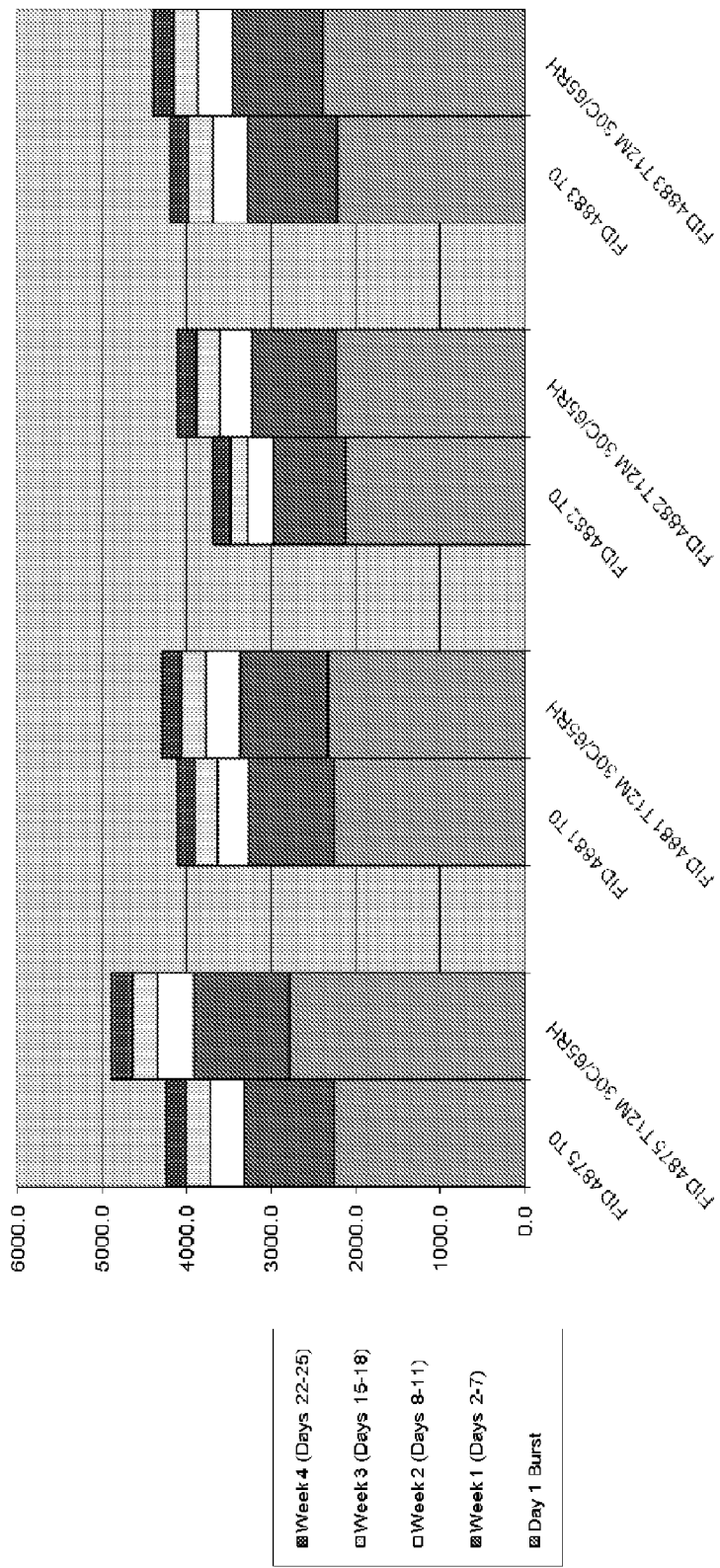
Figure 8: API Cumulative Release at Initial and at 12 Month Storage
*Most drug was released in a burst on Day 1. Cumulative drug release was similar for rings made with each of 4 different silicone bases, at initial and after 12 months of storage.

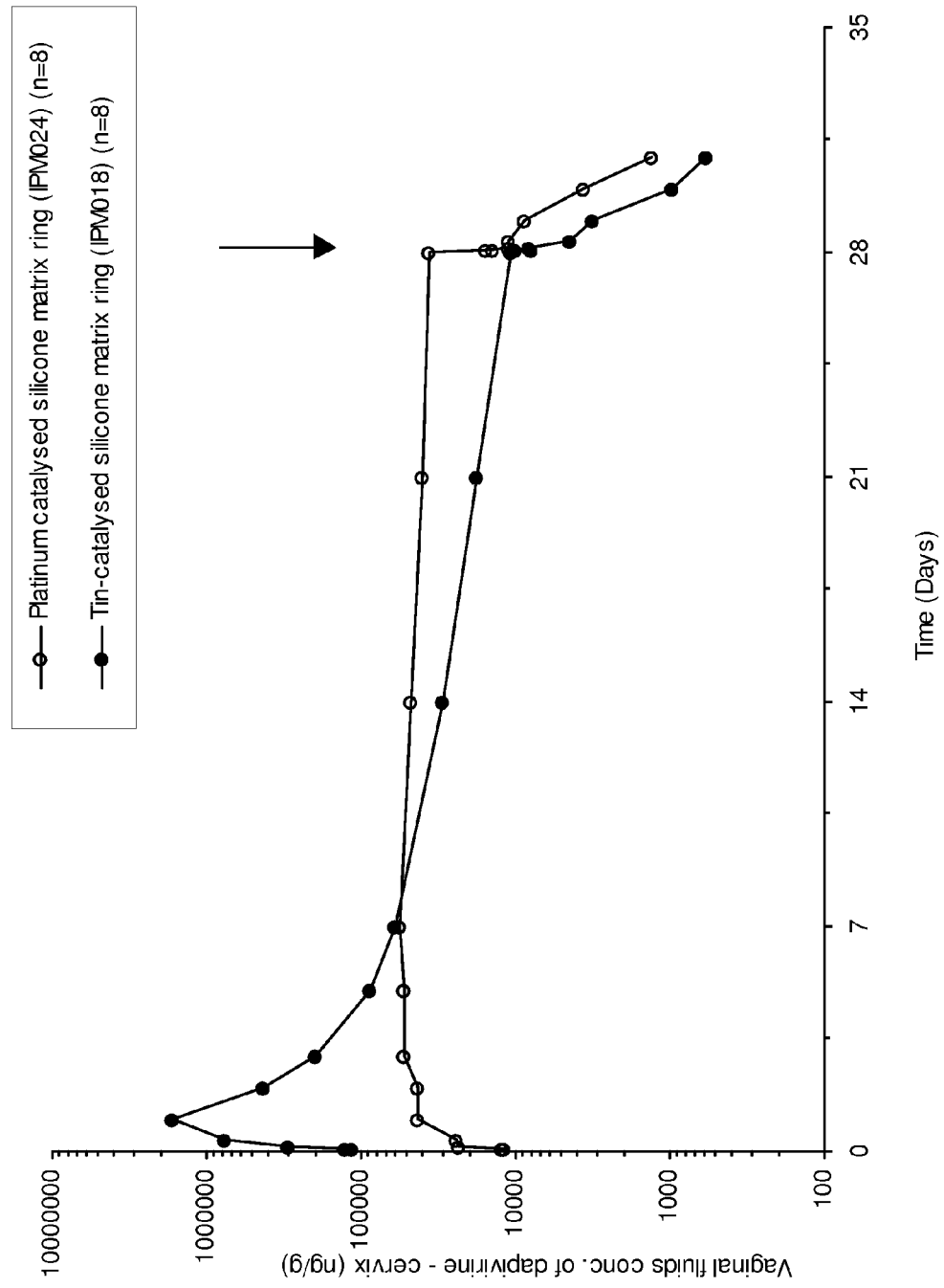
Figure 9: Comparative *In Vivo* Data

PLATINUM-CATALYZED INTRAVAGINAL RINGS

CROSS-REFERENCE TO RELATED APPLICATIONS

This application is a continuation of U.S. application Ser. No. 13/276,454, filed on Oct. 19, 2011, which, in turn, claims priority to U.S. Provisional Application Ser. No. 61/394,493, filed Oct. 19, 2010, the entire contents of each of which are expressly incorporated herein by this reference.

BACKGROUND OF THE INVENTION

The AIDS epidemic continues to exact a devastating toll on the health, economic and political infrastructure, and social fabric of communities worldwide. During 2007, almost 2.5 million people became newly infected with HIV bringing the total number of people living with HIV to an estimated 33.2 million. In the same year almost 2.1 million people died from AIDS, raising the global death toll to over 25 million since the first cases of AIDS were identified in 1981 (UNAIDS and WHO 2007 AIDS Epidemic Update; December 2007). Over 95 percent of new infections are occurring in developing countries where increasing numbers of new HIV infections threaten the sustainability of expanded access to HIV treatment. Developing safe and effective HIV prevention technologies that can be made easily accessible in developing countries is, thus, an urgent public health priority.

Epidemiologic data published in the latest UNAIDS report show that women and girls bear a severe and increasingly heavy burden of the HIV epidemic. In Eastern Europe and Central Asia, an estimated 26% of adults living with HIV in 2007 were women aged 15 years or older, compared with 23% in 2001. In sub-Saharan Africa, women comprised 61% of HIV-infected adults, and among young people (aged 15-24 years) the ratio of infection had risen to three women for every man (UNAIDS and WHO 2007 AIDS Epidemic Update; December 2007).

Unprotected heterosexual intercourse is currently the leading mode of HIV infection among females. Correct and consistent use of latex condoms is one proven method of preventing HIV transmission; however, condoms are widely regarded as inadequate prevention options for women if they are unable to negotiate condom use for fear of abuse or accusations of infidelity. Additionally, women who have sex with men in exchange for gifts or money may be reluctant to use condoms if the men are willing to pay more for sex without a condom. The female condom has been marketed as an alternative barrier method, but this device is relatively costly and requires a certain level of skill, as well as acceptance by the male partner. Developing HIV prevention options that women can use with or without their partner's knowledge is a pressing global concern given the rapidly growing HIV infection rate among women and the absence of an effective vaccine. Topical microbicides that can be self administered to the vagina are one such promising alternative.

Multiple clinical trials with various microbicides have been completed or are currently underway, most of which involve microbicides in gel formulation delivered via a single use applicator used prior to coitus. In order for a microbicide to be effective, it is essential that it be used correctly. Therefore it is important that a microbicide is acceptable to users, and it is likely that products that can be used less frequently will be more acceptable and will achieve better user adherence. Vaginal rings that need only be replaced at relatively long intervals may therefore have benefits over other dosage forms that must be used more frequently. Ring-shaped devices for the controlled administration of steroid substances (substantially water-insoluble drugs) into the vagina are known in the art, such as Estring®, Femring® and Nuvaring®. There are two basic types of vaginal rings: reservoir rings and matrix rings.

The reservoir ring comprises a full or partial-length core loaded with the drug substance, which is completely surrounded by a non-medicated sheath. Accordingly, the release of drug substances from such rings is dependent upon permeation (i.e., molecular dissolution and subsequent diffusion) of the core-loaded drug substance through the outer sheath. Release rates can be modified by changing the thickness of the rate-controlling sheath. Reservoir rings were developed to provide controlled (that is, constant daily) release rates. The polymeric materials used in the construction of commercial vaginal rings are typically hydrophobic silicone elastomer and poly(ethylene-co-vinyl acetate) (PEVA) materials.

In a matrix ring, the drug substance is distributed throughout the device. The combination of high loading and the availability of the drug substance on the surface of the ring device afford relatively high release rates, at least during the initial period after application. Matrix rings are less complicated and expensive to manufacture than reservoir rings. However, there have traditionally been a number of disadvantages associated with this approach. First, it is often cost prohibitive to incorporate potent and expensive therapeutic macromolecules or water-soluble drugs into matrix rings at such high loadings. Second, since release takes place from the surface of the device, a significant proportion of the drug substance within the bulk of the matrix ring is never released, instead being retained within the bulk of the ring itself. Thirdly, a relatively high initial "burst" release of drug substance in the first 24 hours, followed by a declining release rate, has been observed in matrix rings. The matrix design does not allow control over drug release rates through the mechanisms available in reservoir rings.

Accordingly, there remains a need for the development of improved intravaginal rings.

SUMMARY OF THE INVENTION

The present invention provides improved intravaginal drug delivery devices, i.e., intravaginal rings, useful for the administration of therapeutic and/or prophylactic agents to a human. The intravaginal rings of the invention address previous stability issues by utilizing a platinum catalyst (e.g., in the form of a platinum-siloxane complex) for the cross-linking reaction. The vaginal rings of the present invention surprisingly achieve relatively high and steady release rates in vivo with a matrix ring containing a relatively small loading dose. While the matrix rings of the present invention have in vivo the steady release rates associated with reservoir rings, they are easier and less expensive to manufacture.

Additionally, previous attempts to catalyze the instant intravaginal rings resulted in the formation of an alcohol (e.g., propanol) by-product, which continued beyond the manufacture of the ring product, contributing to an increased rate of migration of soluble drug substance (e.g., dapivirine) from within the matrix of the ring to the surface, resulting in crystalline deposits of drug substance on the surface of the rings. However, the present invention provides improved platinum-catalyzed intravaginal rings which do not exhibit alcohol, e.g., propanol, by-product formation, thereby leading to rings which exhibit a constant drug release rate for a prolonged period, e.g., at least one, two, three or four weeks, and display no crystalline surface deposits upon storage.

In one aspect, the invention provides a platinum-catalyzed intravaginal ring comprising an antimicrobial compound, wherein between about 1 mg and about 3 mg of the antimicrobial compound is released in vitro from the ring during an initial 24 hour period of release. In one embodiment, between about 100 and about 500 micrograms of the antimicrobial compound is released in vitro each day for 21 days after an initial 7 day period of release. In another embodiment, use of the ring in vivo results in a steady level of between about 5 micrograms and about 300 micrograms of the antimicrobial compound per gram of vaginal fluid for 24 days after an initial 3 day period of use.

In one embodiment, the intravaginal ring is a matrix-type ring. In another embodiment, the intravaginal ring comprises a silicone polymer. In one embodiment, the antimicrobial compound is homogenously dispersed throughout the ring. In another embodiment, the antimicrobial compound is present in the ring in a therapeutically effective amount. In yet another embodiment, the antimicrobial compound is present in the ring in a prophylactically effective amount.

In one embodiment, about 10 to about 30 mg of the antimicrobial compound is present in the ring. In another embodiment, about 20 to about 30 mg of the antimicrobial compound is present in the ring. In yet another embodiment, about 10 to about 800 mg of the antimicrobial compound is present in the ring. In another embodiment, about 25 mg of the antimicrobial compound is present in the ring.

In one embodiment, antimicrobial compound release rates are stable following 3 months of storage. In another embodiment, antimicrobial compound release rates are stable following 6 months of storage. In another embodiment, antimicrobial compound release rates are stable following 12 months of storage. In yet another embodiment, antimicrobial compound release rates are stable following 36 months of storage.

In one embodiment, no crystalline deposits of antimicrobial compound are formed on the surface of the ring. In another embodiment, the ring does not contain alcohol by-products. In yet another embodiment, the ring does not contain propanol by-products.

In one embodiment, the antimicrobial compound is a non-nucleoside reverse transcriptase inhibitor (NNRTI). In one embodiment, the NNRTI is a substituted di-amino-pyrimidine derivative. In another embodiment, the di-amino-pyrimidine derivative is dapivirine.

In one embodiment, the intravaginal ring has an outer diameter of 56 mm. In another embodiment, the intravaginal ring has a cross-sectional diameter of 7.6 mm.

In another aspect, the invention provides a platinum-catalyzed intravaginal ring comprising dapivirine, wherein the ring is a matrix-type ring. In one embodiment, between about 1 mg and about 3 mg of dapivirine is released in vitro from the ring during an initial 24 hour period of release. In another embodiment, between about 100 micrograms and about 500 micrograms of dapivirine is released in vitro each day for 21 days after an initial 7 day period of release. In yet another embodiment, use of the ring in vivo results in a steady level of between about 5 micrograms and about 300 micrograms of dapivirine per gram of vaginal fluid for 24 days after an initial 3 day period of use.

In one embodiment, the intravaginal ring comprises a silicone polymer. In another embodiment, the dapivirine is homogenously dispersed throughout the ring. In yet another embodiment, the dapivirine is present in the ring in a therapeutically effective amount. In another embodiment, the dapivirine is present in the ring in a prophylactically effective amount.

In one embodiment, about 10 to about 30 mg of the dapivirine is present in the ring. In another embodiment, about 20 to about 30 mg of the dapivirine is present in the ring. In another embodiment, about 10 to about 800 mg of the dapivirine is present in the ring. In one embodiment, about 25 mg of the dapivirine is present in the ring.

In one embodiment, dapivirine release rates are stable following 3 months of storage. In another embodiment, dapivirine release rates are stable following 6 months of storage. In another embodiment, dapivirine release rates are stable following 12 months of storage. In yet another embodiment, dapivirine release rates are stable following 36 months of storage.

In one embodiment, no crystalline deposits of dapivirine are formed on the surface of the ring. In another embodiment, the ring does not comprise alcohol by-products. In another embodiment, the ring does not contain propanol by-products.

In one embodiment, the intravaginal ring has an outer diameter of 56 mm. In another embodiment, the intravaginal ring has a cross-sectional diameter of 7.6 mm.

In another aspect, the invention provides a platinum-catalyzed intravaginal ring comprising an antimicrobial compound, wherein between about 5 micrograms and about 300 micrograms of the antimicrobial compound are released in vivo from the ring per gram of vaginal fluid for 24 days after an initial 3 day period of use.

In one embodiment, the intravaginal ring comprises a silicone polymer. In another embodiment, the antimicrobial compound is homogenously dispersed throughout the ring. In another embodiment, the antimicrobial compound is present in the ring in a therapeutically effective amount. In another embodiment, the antimicrobial compound is present in the ring in a prophylactically effective amount.

In one embodiment, about 10 to about 30 mg of the antimicrobial compound is present in the ring. In another embodiment, about 20 to about 30 mg of the antimicrobial compound is present in the ring. In yet another embodiment, about 10 to about 800 mg of the antimicrobial compound is present in the ring. In another embodiment, about 25 mg of the antimicrobial compound is present in the ring.

In one embodiment, antimicrobial compound release rates are stable following 3 months of storage. In another embodiment, antimicrobial compound release rates are stable following 6 months of storage. In another embodiment, antimicrobial compound release rates are stable following 12 months of storage. In yet another embodiment, antimicrobial compound release rates are stable following 36 months of storage.

In one embodiment, no crystalline deposits of antimicrobial compound are formed on the surface of the ring. In another embodiment, the ring does not comprise alcohol by-products. In another embodiment, the ring does not contain propanol by-products.

In one embodiment, the intravaginal ring has an outer diameter of 56 mm. In another embodiment, the intravaginal ring has a cross-sectional diameter of 7.6 mm.

In another embodiment, between about 10 micrograms and about 100 micrograms of the antimicrobial compound are released in vivo from the ring per gram of vaginal fluid for 24 days after an initial 3 day period of use. In yet another embodiment, between about 20 micrograms and about 80 micrograms of the antimicrobial compound are released in vivo from the ring per gram of vaginal fluid for 24 days after an initial 3 day period of use.

In another embodiment, the antimicrobial compound is a non-nucleoside reverse transcriptase inhibitor (NNRTI). In another embodiment, the NNRTI is a substituted di-amino-pyrimidine derivative. In one embodiment, the di-amino-pyrimidine derivative is dapivirine.

In another aspect the invention provides a method of blocking DNA polymerization by an HIV reverse transcriptase enzyme in a female human, comprising the step of inserting the intravaginal ring of the invention into the vagina of the female human.

In another aspect, the invention provides a method of preventing HIV infection in a female human, comprising the step of inserting the intravaginal ring of the invention into the vagina of the female human.

In yet another aspect, the invention provides method of treating HIV infection in a female human, comprising the step of inserting the intravaginal ring of the invention into the vagina of the female human.

Other features and advantages of the invention will be apparent from the following detailed description and claims.

BRIEF DESCRIPTION OF THE DRAWINGS

FIG. 3 depicts the formulation matrix of several different platinum-catalyzed intravaginal rings which each have a different silicone elastomer base material.

FIG. 4 depicts a typical API chromatogram for dapivirine.

FIG. 5 depicts variability in cumulative API release (mcg) for rings produced from different silicone elastomer base materials.

FIG. 6 depicts the API cumulative daily release of antimicrobial agent from rings produced from different silicone elastomer base materials as a function of the square root of time.

FIG. 7 depicts the API daily antimicrobial agent release rate for intravaginal rings initially and after twelve months of storage. In general, daily release profiles did not change significantly following storage of rings for twelve months.

FIG. 8 depicts the API cumulative antimicrobial agent release rate for intravaginal rings made from four different silicone bases, both initially and after twelve months of storage.

FIG. 9 is a graph depicting comparative in vivo release data using the rings of the invention. In the first study, eight women used tin catalyzed silicone rings containing 25 mg of dapivirine for 28 days. In the second study, eight women used platinum catalyzed silicone rings containing 25 mg of dapivirine for 28 days. In both studies, samples of cervical fluids were taken five times during the first 24 hours after insertion, daily for the remainder of the first week, and weekly thereafter until removal of the ring. Samples of cervical fluid were analyzed to determine the level of dapivirine present in the cervical fluid on the date of each sample.

DETAILED DESCRIPTION OF THE INVENTION

Figure 1:
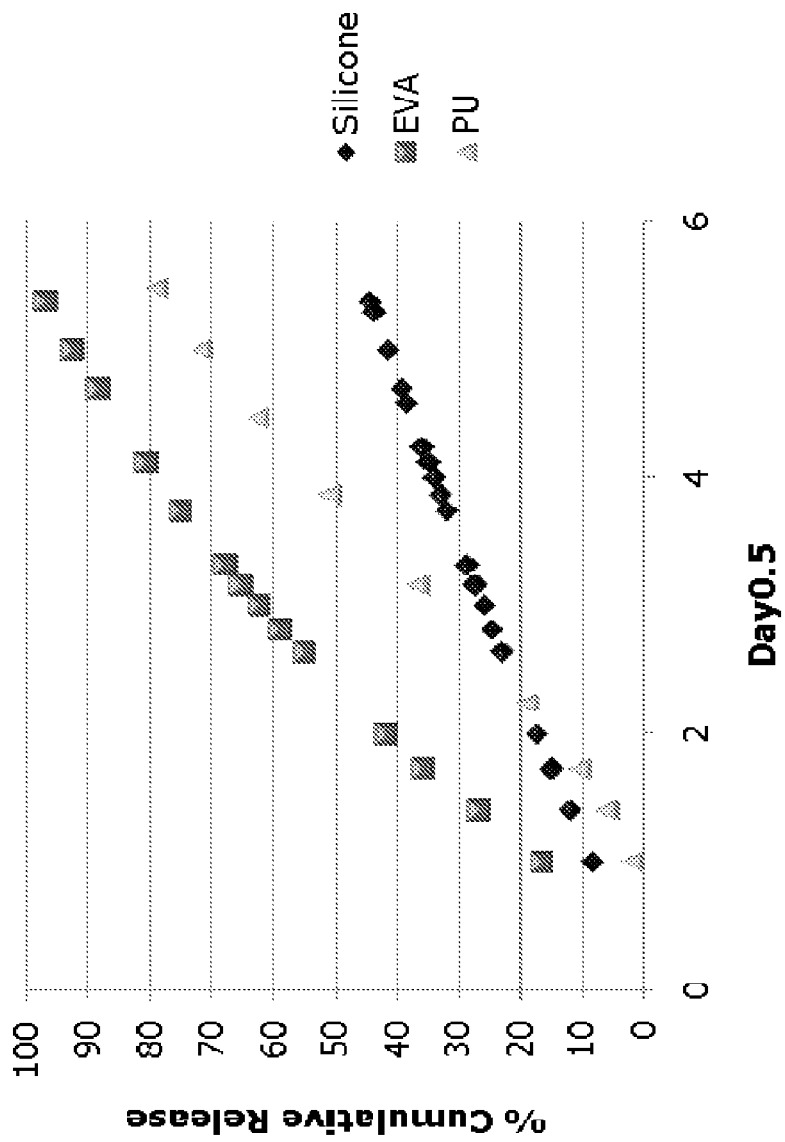
FIG. 1 depicts the percent cumulative release of dapivirine from various polymers, such as silicone, EVA and polyurethane (PU).

The present invention provides improved intravaginal drug delivery devices, i.e., intravaginal rings, useful for the administration of therapeutic and/or prophylactic agents to a human. The intravaginal rings of the invention address previous stability issues by utilizing an organo-platinum catalyst (e.g., in the form of a platinum-siloxane complex) for the cross-linking reaction. The vaginal rings of the present invention surprisingly achieve relatively high and steady release rates in vivo with a matrix ring containing a relatively small loading dose. While the matrix rings of the present invention have in vivo the steady release rates associated with reservoir rings, they are easier and less expensive to manufacture.

As used herein, the term "intravaginal ring" or "vaginal ring" refers to a doughnut-shaped polymeric drug delivery device which is designed to be inserted into the vagina of a female human in order to provide controlled release of drugs to the vagina over an extended period of time. Several intravaginal rings are currently available, including Estring® and Femring®, for the treatment of urogenital symptoms of post-menopause, and NuvaRing®, a contraceptive vaginal ring.

The intravaginal rings of the instant invention provide controlled release of antimicrobial compounds and may have any shape and be of any dimensions compatible with intravaginal administration to a female human. Such a ring can be self-inserted high into the vagina, where it is held in place due to its shape and inherent elasticity.

Such intravaginal rings permit single intravaginal dosing of an antimicrobial agent(s), with an initially high "loading" and a subsequent, lower "maintenance" release profile. In addition, such a device provides high user adherence, ease of application and exhibits no leakage or messiness on insertion and subsequent placement within the vaginal space.

As used herein, the term "platinum-catalyzed" refers to an intravaginal ring whose cross-linking reaction has been catalyzed using an organo-platinum compound. In one embodiment, the intravaginal ring comprises a silicone elastomer. In yet another embodiment, the intravaginal ring comprises a silicone elastomer and a silicone dispersant. The intravaginal ring may comprise other pharmaceutically compatible agents. Such agents include pharmacologically active agents, as well as, pharmacologically inactive agents known in the art as pharmaceutical excipients.

As used herein, the term "matrix ring" or "matrix-type ring" refers to an intravaginal ring in which the antimicrobial agent is homogenously distributed throughout the ring. Matrix rings are typically manufactured by injection molding or extrusion of an antimicrobial compound-containing active mix, leading to the uniform distribution of the antimicrobial compound throughout the ring. The matrix-type rings of the instant invention may comprise dapivirine dispersed in silicone elastomer with normal propylorthosilicate (NPOS) crosslinker. This active mix is subsequently cured using a catalyst, such as platinum (with curing achieved by an addition reaction).

In one embodiment, about 10 to about 30 mg of the antimicrobial compound is present in the ring. In another embodiment, about 20 mg to about 30 mg of the antimicrobial compound is present in the ring. In yet another embodiment, about 10 to about 800 mg, about 50 mg to about 750 mg, about 100 mg to about 700 mg, or about 200 mg to about 600 mg, about 300 mg to about 400 mg of the antimicrobial compound is present in the ring.

In another embodiment, about 25 mg of the antimicrobial compound is present in the ring. In another embodiment, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 90 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, or about 800 mg of the antimicrobial compound is present in the ring.

As used herein, the term "reservoir ring" refers to an intravaginal ring in which an antimicrobial agent is dispersed in a reservoir, a full or partial-length core loaded with the drug substance, which is completely surrounded by a non-medicated sheath. Accordingly, the release of drug substances from such rings is dependent upon permeation (i.e., molecular dissolution and subsequent diffusion) of the core-loaded drug substance through the outer sheath. Release rates can be modified by changing the nature or thickness of the rate-controlling sheath. Reservoir rings were developed to provide controlled (that is, constant daily) release rates.

As used herein, the term "antimicrobial compound" or "antimicrobial agent" (used interchangeably herein) refers to a compound or agent which is capable of inhibiting or destroying the growth of a microbial organism. In a preferred embodiment of the invention, the antimicrobial compound is a non-nucleoside reverse transcriptase inhibitor ("NNRTI"). In another embodiment, the NNRTI is a substituted di-amino pyrimidine derivative. In yet another embodiment, the di-amino-pyrimidine derivative is dapivirine. The term "antimicrobial compound" is intended to embrace antibacterial agents, antifungal agents, antiprotozoal agents, antiviral agents and mixtures thereof.

Mixtures of antibacterial agents, mixtures of antifungal agents; mixtures of antiviral agents; mixtures of antiprotozoal agents and mixtures of agents from two or more of these categories are also envisaged by the present invention. In addition, it is also envisaged that the present invention embraces at least one antimicrobial agent (microstatic and/or microcidal agent) with one or more other pharmaceutically active agent.

As used herein, the term "dapivirine" refers to (4-[[4-[(2,4,6-trimethylphenyl)amino]-2-pyrimidinyl]amino]benzonitrile), a non-nucleoside reverse transcriptase inhibitor. Dapivirine is useful in the prevention and/or treatment of retroviral infection, such as HIV-1 infection. It is a crystalline compound that is white to slightly beige in color, has a melting point of about 220° C. and is virtually insoluble in water. More specifically, the solubility of dapivirine is less than 0.001 mg/gm of water (i.e., less than 1 µg/ml of water). The intravaginal rings of the instant invention may use micronized dapivirine. A composite result (four samples taken of micronized material) showed that 88.15% of the material had a particle size of less than 5 microns (µM).

Various aspects of the invention are described in further detail in the following subsections:

I. Intravaginal Rings

The present invention provides improved intravaginal drug delivery devices, i.e., intravaginal rings, useful for the administration of therapeutic and/or prophylactic agents to a human. The intravaginal rings of the invention address previous stability issues by utilizing a platinum catalyst (e.g., in the form of a platinum-siloxane complex) for the cross-linking, e.g., silicone cross-linking, reaction. The vaginal rings of the present invention surprisingly achieve relatively high and steady release rates in vivo with a matrix ring containing a relatively small loading dose. As used herein, the term "intravaginal ring" or "vaginal ring" refers to a doughnut-shaped polymeric drug delivery device which is designed to be inserted into the vagina of a female human in order to provide controlled release of drugs to the vagina over an extended period of time. Several intravaginal rings are currently available, including Estring® and Femring®, for the treatment of urogenital symptoms of post-menopause, and NuvaRing®, a contraceptive vaginal ring. Intravaginal rings are described in U.S. Pat. No. 6,951,654, U.S. Patent Application Publication Nos. US2007/0043332 and US2009/0004246, PCT Publication Nos. WO99/50250, WO02/076426 and WO03/094920, the entire contents of each of which are expressly incorporated herein by reference.

The intravaginal rings of the instant invention provide controlled release of antimicrobial compounds and may have any shape and be of any dimensions compatible with intravaginal administration to a female human. Such a ring can be self-inserted into the vagina, where it is held in place due to its shape and inherent elasticity. In one embodiment, the intravaginal ring has an outer diameter of 56 mm. In another embodiment, the intravaginal ring has an outer diameter of about 50 mm, about 51 mm, about 52 mm, about 53 mm, about 54 mm, about 55 mm, about 56 mm, about 57 mm, about 58 mm, about 59 mm or about 60 mm. In another embodiment, the intravaginal ring has a cross-sectional diameter of 7.7 mm. In yet another embodiment, the intravaginal ring has a cross-sectional diameter of about 7.0 mm, about 7.1 mm, about 7.2 mm, about 7.3 mm, about 7.4 mm, about 7.5 mm, about 7.6 mm, about 7.7 mm, about 7.8 mm, about 7.9 mm, about 8.0 mm, about 8.1 mm, about 8.2 mm, about 8.3 mm, about 8.4 mm, or about 8.5 mm.

Such an intravaginal rings permits single intravaginal dosing of an antimicrobial agent(s), with a stable release profile. In addition, a device that can be applied less frequently is likely be more acceptable and to achieve better adherence relative to gels that need to be used more frequently In one embodiment, the intravaginal ring comprises a silicone elastomer. In yet another embodiment, the intravaginal ring comprises a silicone elastomer and a silicone dispersant.

The intravaginal ring may comprise other pharmaceutically compatible agents. Such agents include pharmacologically active agents, as well as, pharmacologically inactive agents known in the art as pharmaceutical excipients. Examples of pharmacologically active agents that may be advantageous include, but are not limited to, a local anesthetic such as lidocaine or a local analgesic or a mixture thereof. Examples of pharmacologically inactive agents that may be advantageous include, but are not limited to, a buffer (or buffers), or hydrophilic compounds that enhance the rate of release of the agent from the device, such as for example, polyvinylpyrrolidone (PVP or povidone), modified cellulose ethers (e.g., hydroxyethylcellulose, hydroxypropylcellulose and hydroxypropylmethylcellulose) microcrystalline cellulose, polyacrylic acid, carbomer, alginic acid, carrageenan, cyclodextrins, dextrin, guar gum, gelatin, xanthan gum and sugars (e.g., monosaccharides such as glucose, fructose and galactose, and disaccharides such as lactose, maltose and fructose). When employed, the release rate enhancing excipient is generally present in an amount of about 0.5 to about 40 w/w % and preferably about 2.5 to about 15 w/w % of the device.

As used herein, the term "matrix ring" or "matrix-type ring" refers to an intravaginal ring in which the antimicrobial agent is homogenously distributed throughout the ring. Matrix rings are typically manufactured by injection molding or extrusion of an antimicrobial compound-containing active mix, leading to the uniform distribution of the antimicrobial compound throughout the ring. The matrix-type rings of the instant invention may comprise dapivirine dispersed in silicone elastomer with normal propylorthosilicate (NPOS) crosslinker. This active mix is subsequently cured using a catalyst, such as platinum (with curing achieved by an addition reaction).

As used herein, the term "reservoir ring" refers to an intravaginal ring in which an antimicrobial agent is dispersed in a reservoir, a full or partial-length core loaded with the drug substance, which is completely surrounded by a non-medicated sheath. Accordingly, the release of drug substances from such rings is dependent upon permeation (i.e., molecular dissolution and subsequent diffusion) of the core-loaded drug substance through the outer sheath. Release rates can be modified by changing the nature or thickness of the rate-controlling sheath. Reservoir rings were developed to provide controlled (that is, constant daily) release rates.

As used herein, the term "elastomer" refers to an amorphous polymer network formed when a polymer or a mixture of polymers undergo cross-linking. Each polymer is comprised of monomeric units, which are linked together to form the polymer. The monomeric units can comprise carbon, hydrogen, oxygen, silicon, halogen, or a combination thereof.

In some embodiments, the intravaginal ring comprises a polysiloxane. As used herein, a "polysiloxane" refers to any of various compounds containing alternate silicon and oxygen atoms in either a linear or cyclic arrangement usually with one or two organic groups attached to each silicon atom. For example, polysiloxanes include substituted polysiloxanes, and diorganopolysiloxanes such as diarylpolysiloxanes and dialkylpolysiloxanes; an example of the latter is dimethylpolysiloxane. Such dimethylpolysiloxane polymers can be thermoset to the corresponding elastomer by vulcanization with peroxide curing catalysts, e.g., benzoyl peroxide or di-p-chlorobenzoyl peroxide at temperatures of about 200° C. and requiring additional heat after treatment as described in U.S. Pat. Nos. 2,541,137; 2,723,966; 2,863, 846; 2,890,188; and 3,022,951, the entire contents of each of which are expressly incorporated herein by reference.

An example of a two-component silicone elastomer, which is platinum-catalyzed at room temperature or under slightly elevated temperature and capable of cross-linking, is MED-4870 (NuSil Technology LLC, Carpinteria, Calif.). In some embodiments of the present invention, an intravaginal ring can comprise silicone liquid (NuSil MED360) as a dispersing agent, and NuSil MED-4870 elastomer. The MED-4870 elastomer is composed of two parts, part A and part B. The chemical composition of MED-4870 part A comprises vinyl terminated polydimethylsiloxane (linear) polymers as a polymer, platinum-siloxane complex as the catalyst for the cross-linking reaction, and ~30% amorphous (non crystalline) reinforcing silica as a filler. The chemical composition of MED-4870 part B comprises vinyl-terminated polydimethylsiloxane (linear) polymers, hydride functional polydimethysiloxane polymer as a cross-linker, and ~30% amorphous (non-crystalline) reinforcing silica as a filler. Form A and form B undergo cross-linking to form a silicone elastomer.

In some embodiments of the present invention, the polysiloxane elastomer is a diorganopolysiloxane elastomer. In some embodiments, the diorganopolysiloxane elastomer is dimethylpolysiloxane elastomer. In some embodiments, the dimethylpolysiloxane elastomer further comprises a dimethylmethylhydrogen polysiloxane cross-link. In some embodiments of the present invention, the polysiloxane elastomer is MED-4870.

In some embodiments, the polysiloxane elastomer is present in a concentration of about 90% to about 99% by total weight of the ring. In some embodiments, the polysiloxane elastomer is present in a concentration of about 95% by total weight of the ring, or about 97% by total weight of the ring.

Suitable cross-linking agents and curing catalysts are well known in the art. Curing temperatures and times will vary, depending on the particular elastomer(s) used. For example, the curing temperature may vary between room temperature (15-25° C.) and 150° C. but is preferably within the range 60-100° C. The curing time may vary between a few seconds and several hours, depending on the elastomer(s) used. Preferred and suitable elastomers include two-component dimethylpolysiloxane compositions using platinum as the curing catalyst and at a curing temperature of from room temperature to an elevated temperature.

As used herein, the term "platinum-catalyzed" refers to an intravaginal ring whose cross-linking reaction has been catalyzed using an organo-platinum compound.

As used herein, the term "alcohol by-product" refers to a volatile by-product of alcohol (including propanol) produced by tin-catalyzed condensation reactions for cross-linking of solid state silicone. Alcohol by-product contributes to an increased rate of migration of antimicrobial compound from within the matrix of an intravaginal ring to the surface, resulting in the undesirable formation of crystalline deposits of antimicrobial compound on the intravaginal ring.

As used herein, the term "crystalline deposits" refers to the undesirable formation of deposits of crystals of the antimicrobial compound on the surface of the intravaginal ring.

As used herein, the term "release" or "release rate" refers to the amount or concentration of antimicrobial agent which leaves the intravaginal ring in any defined time period. "Sustained release" or "sustained release rate" refers to release sufficient to provide antimicrobial properties over a specific time period. For example, in one embodiment of the invention, the intravaginal rings are designed to provide sustained release of the antimicrobial compound. In a preferred embodiment of the invention, between about 1 mg and about 3 mg of the antimicrobial compound is released in vitro during an initial 24 hour period of release. In one embodiment, less than 1 mg of the antimicrobial compound is released in vitro each day for 21 days after an initial 7 day period of release. In one embodiment, about 100 micrograms to about 500 micrograms of the antimicrobial compound is released in vitro each day for 21 days after an initial 7 day period of release. In another embodiment, about 100 micrograms, about 125 micrograms, about 150 micrograms, about 175 micrograms, about 200 micrograms, about 225 micrograms, about 250 micrograms, about 275 micrograms, about 300 micrograms, about 350 micrograms, about 400 micrograms, about 450 micrograms or about 500 micrograms of the antimicrobial compound is released each day for 21 days after an initial 7 day period of release.

In another embodiment, between about 5 micrograms and about 300 micrograms of the antimicrobial compound is released in vivo per gram of vaginal fluid each day for 24 days after an initial 3 day period of use. In another embodiment, between about 10 micrograms and about 100 micrograms of the antimicrobial compound is released in vivo per gram of vaginal fluid each day for 24 days after an initial 3 day period of use. In another embodiment, between about 20 micrograms and about 80 micrograms of the antimicrobial compound is released in vivo per gram of vaginal fluid each day for 24 days after an initial 3 day period of use. In yet another embodiment, about 5 micrograms, about 10 micrograms, about 25 micrograms, about 50 micrograms, about 75 micrograms, about 100 micrograms, about 125 micrograms, about 150 micrograms, about 175 micrograms, about 200 micrograms, about 225 micrograms, about 250 micrograms, about 275 micrograms, about 300 micrograms, about 350 micrograms, about 400 micrograms, about 450 micrograms, about 500 micrograms, or about 600 micrograms of the antimicrobial compound is released in vivo per gram of vaginal fluid each day for 24 days after an initial 3 day period of use. Values and ranges included and/or intermediate within the ranges set forth herein are also intended to be within the scope of the present disclosure. Ranges having values recited herein as an upper or lower limit are also intended to be within the scope of the present disclosure. Moreover, the amount of antimicrobial compound released may clearly be varied depending on, for example, the desired dosing level, the particular antimicrobial compound, the release rate effect of excipients used in the device, and the particular elastomeric system employed.

As used herein, the term "initial 24 hour period of use" refers to the first day, or twenty-four hours, of time after the initial use of the intravaginal ring. The initial 24 hour period of use begins when the intravaginal ring is inserted into the vagina of the female human.

As used herein, the term "each day" refers to an individual 24 hour period.

As used herein, the term "homogenously dispersed throughout" refers to an antimicrobial compound which is uniformly distributed throughout the intravaginal ring.

As used herein, the term "prophylactically effective amount" refers to the amount of antimicrobial compound effective to prevent development of disease in the subject. In one embodiment of the invention, the disease is HIV. In a preferred embodiment of the invention, a prophylactically effective amount is achieved when between about 1 mg and about 3 mg of the antimicrobial compound is released in vitro during an initial 24 hour period of release. In one embodiment of the invention, a prophylactically effective amount is achieved when between about 100 micrograms to about 500 micrograms of the antimicrobial compound is released in vitro per day after the initial 7 day period of release. In one embodiment of the invention, a prophylactically effective amount is achieved when between about 200 micrograms to about 400 micrograms of the antimicrobial compound is released in vitro per day after the initial 7 day period of release. In another embodiment of the invention, a prophylactically effective amount is achieved when between about 250 micrograms to about 350 micrograms of the antimicrobial compound is released in vitro per day after the initial 7 day period of release. In another embodiment of the invention, a prophylactically effective amount is achieved when between about 300 micrograms to about 400 micrograms of the antimicrobial compound is released in vitro per day after the initial 7 day period of release. In one embodiment, a prophylactically effective amount is achieved when about 50 micrograms, about 100 micrograms, about 125 micrograms, about 150 micrograms, about 175 micrograms, about 200 micrograms, about 225 micrograms, about 250 micrograms, about 275 micrograms, about 300 micrograms, about 325 micrograms, about 350 micrograms, about 375 micrograms, about 400 micrograms, about 450 micrograms, about 475 micrograms, about 500 micrograms, about 550 micrograms, about 600 micrograms, about 650 micrograms, about 700 micrograms, about 750 micrograms, about 800 micrograms, about 850 micrograms, about 900 micrograms about 950 micrograms, about 1 mg, less than 1 mg or more than 1 mg of the antimicrobial compound is released in vitro per day after the initial 7 day period of release.

In another embodiment, a prophylactically effective amount is achieved when between about 5 micrograms and about 300 micrograms of the antimicrobial compound is released in vivo per gram of vaginal fluid each day for 24 days after an initial 3 day period of use. In another embodiment, a prophylactically effective amount is achieved when between about 10 micrograms and about 100 micrograms of the antimicrobial compound is released in vivo per gram of vaginal fluid each day for 24 days after an initial 3 day period of use. In another embodiment, a prophylactically effective amount is achieved when between about 20 micrograms and about 80 micrograms of the antimicrobial compound is released in vivo per gram of vaginal fluid each day for 24 days after an initial 3 day period of use. In yet another embodiment, a prophylactically effective amount is achieved when about 5 micrograms, about 10 micrograms, about 25 micrograms, about 50 micrograms, about 75 micrograms, about 100 micrograms, about 125 micrograms, about 150 micrograms, about 175 micrograms, about 200 micrograms, about 225 micrograms, about 250 micrograms, about 275 micrograms, about 300 micrograms, about 350 micrograms, about 400 micrograms, about 450 micrograms, about 500 micrograms, or about 600 micrograms of the antimicrobial compound is released in vivo per gram of vaginal fluid each day for 24 days after an initial 3 day period of use.

Values and ranges included and/or intermediate within the ranges set forth herein are also intended to be within the scope of the present disclosure. Ranges having values recited herein as an upper or lower limit are also intended to be within the scope of the present disclosure.

As used herein, the term "therapeutically effective amount" refers to the amount of antimicrobial compound effective to treat disease in the subject. In one embodiment of the invention, the disease is HIV. In a preferred embodiment of the invention, a therapeutically effective amount is achieved when between about 1 mg and about 3 mg of the antimicrobial compound is released in vitro during an initial 24 hour period of release. In one embodiment of the invention, a therapeutically effective amount is achieved when between about 100 micrograms to about 500 micrograms of the antimicrobial compound is released in vitro per day after the initial 7 day period of release. In one embodiment of the invention, a therapeutically effective amount is achieved when between about 200 micrograms to about 400 micrograms of the antimicrobial compound is released in vitro per day after the initial 7 day period of release. In another embodiment of the invention, a therapeutically effective amount is achieved when between about 250 micrograms to about 350 micrograms of the antimicrobial compound is released in vitro per day after the initial 7 day period of release. In another embodiment of the invention, a therapeutically effective amount is achieved when between about micrograms to about 400 micrograms of the antimicrobial compound is released in vitro per day after the initial 7 day period of release. In one embodiment, a therapeutically effective amount is achieved when about 100 micrograms, about 125 micrograms, about 150 micrograms, about 175 micrograms, about 200 micrograms, about 225 micrograms, about 250 micrograms, about 275 micrograms, about 300 micrograms, about 325 micrograms, about 350 micrograms, about 375 micrograms, about 400 micrograms, about 450 micrograms, about 475 micrograms, or about 500 micrograms of the antimicrobial compound is released in vitro per day after the initial 7 day period of release.

In another embodiment, a therapeutically effective amount is achieved when between about 5 micrograms and about 300 micrograms of the antimicrobial compound is released in vivo per gram of vaginal fluid each day for 24 days after an initial 3 day period of use. In another embodiment, a therapeutically effective amount is achieved when between about 10 micrograms and about 100 micrograms of the antimicrobial compound is released in vivo per gram of vaginal fluid each day for 24 days after an initial 3 day period of use. In another embodiment, a therapeutically effective amount is achieved when between about 20 micrograms and about 80 micrograms of the antimicrobial compound is released in vivo per gram of vaginal fluid each day for 24 days after an initial 3 day period of use. In yet another embodiment, a therapeutically effective amount is achieved when about 5 micrograms, about 10 micrograms, about 25 micrograms, about 50 micrograms, about 75 micrograms, about 100 micrograms, about 125 micrograms, about 150 micrograms, about 175 micrograms, about 200 micrograms, about 225 micrograms, about 250 micrograms, about 275 micrograms, about 300 micrograms, about 350 micrograms, about 400 micrograms, about 450 micrograms, about 500 micrograms, or about 600 micrograms of the antimicrobial compound is released in vivo per gram of vaginal fluid each day for 24 days after an initial 3 day period of use.

Values and ranges included and/or intermediate within the ranges set forth herein are also intended to be within the scope of the present disclosure. Ranges having values recited herein as an upper or lower limit are also intended to be within the scope of the present disclosure.

As used herein, the term "controlled release rate" refers to a constant release rate that can be determined by the design and drug loading of the vaginal ring.

As used herein, the term "constant release rate" refers to a release rate which does not readily change with device storage over time. Preferably, the release rate of the antimicrobial compound from the intravaginal ring is constant, or stable and does not readily change over time at room temperature (about 30° C.) or at 40° C. for at least 1 month, at about 2-8° C. for at least 1 year, or for at least 2 years. For example, the release rate of the antimicrobial compound from the intravaginal rings of the instant invention can be stable for 1, 2, 3, 4, 5, 6, 7, 8, 9, 10, 11, 12, 13, 14, 15, 16, 17, 18, 19, 20, 21, 22, 23, 24, 30, 36, 42 or 48 months.

As used herein, the term "steady release rate" means a release rate that shows relatively little change over time.

A "stable" antimicrobial compound is one which essentially retains its physical stability and/or chemical stability and/or biological activity during the manufacturing process and/or upon storage. Various analytical techniques for measuring stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993).

As used herein, the term "storage" refers to the period of time after which the intravaginal rings are made, but before which the intravaginal rings are used. For example, the intravaginal rings of the instant invention can be stored for 1, 2, 3, 4, 5, 6, 7, 8, 9, 10, 11, 12, 13, 14, 15, 16, 17, 18, 19, 20, 21, 22, 23, 24, 30, 36, 42 or 48 months.

II. Antimicrobial Compounds

As used herein, the term "antimicrobial compound" or "antimicrobial agent" (used interchangeably herein) refers to a compound or agent which is capable of inhibiting or destroying the growth of a microbial organism. In a preferred embodiment of the invention, the antimicrobial compound is a non-nucleoside reverse transcriptase inhibitor ("NNRTI"). In another embodiment, the NNRTI is a substituted di-amino pyrimidine derivative. In yet another embodiment, the di-amino-pyrimidine derivative is dapivirine. In another preferred embodiment of the invention, a combination of an NNRTI and an entry inhibitor is used. In another embodiment, the NNRTI is dapivirine and the entry inhibitor is maraviroc. In another preferred embodiment of the invention, a combination of an NNRTI and a nucleoside reverse transcriptase inhibitor is used.

The term "antimicrobial compound" is intended to embrace antibacterial agents, antifungal agents, antiprotozoal agents, antiviral agents and mixtures thereof.

Suitable antibacterial agents include Acrosoxacin, Amifloxacin, Amoxycillin, Ampicillin, Aspoxicillin, Azidocillin, Azithromycin, Aztreonam, Balofloxacin, Benzylpenicillin, Biapenem, Brodimoprim, Cefaclor, Cefadroxil, Cefatrizine, Cefcapene, Cefdinir, Cefetamet, Cefinetazole, Cefprozil, Cefroxadine, Ceftibuten, Cefuroxime, Cephalexin, Cephalonium, Cephaloridine, Cephamandole, Cephazolin, Cephradine, Chlorquinaldol, Chlortetracycline, Ciclacillin, Cinoxacin, Ciprofloxacin, Clarithromycin, Clavulanic Acid, Clindamycin, Clofazimine, Cloxacillin, Danofloxacin, Dapsone, Demeclocycline, Dicloxacillin, Difloxacin, Doxycycline, Enoxacin, Enrofloxacin, Erythromycin, Fleroxacin, Flomoxef, Flucloxacillin, Flumequine, Fosfomycin, Isoniazid, Levofloxacin, Mandelic Acid, Mecillinam, Metronidazole, Minocycline, Mupirocin, Nadifloxacin, Nalidixic Acid, Nifuirtoinol, Nitrofurantoin, Nitroxoline, Norfloxacin, Ofloxacin, Oxytetracycline, Panipenem, Pefloxacin, Phenoxymethylpenicillin, Pipemidic Acid, Piromidic Acid, Pivampicillin, Pivmecillinam, Prulifloxacin, Rufloxacin, Sparfloxacin, Sulbactam, Sulfabenzamide, Sulfacytine, Sulfametopyrazine, Sulphacetamide, Sulphadiazine, Sulphadimidine, Sulphamethizole, Sulphamethoxazole, Sulphanilamide, Sulphasomidine, Sulphathiazole, Temafloxacin, Tetracycline, Tetroxoprim, Timidazole, Tosufloxacin, Trimethoprim and salts or esters thereof.

Preferred antibacterial agents include tetracyclines such as Doxycycline, Tetracycline or Minocycline; macrolides such as Azithromycin, Clarithromycin and Erythromycin; nitroimidazoles such as Metronidazole or Timidazole; quinolones such as Ofloxacin, Norfloxacin, Cinoxacin, Ciprofloxacin and Levofloxacin; Clindamycin and Dapsone.

Suitable antifungal agents include Bifonazole, Butoconazole, Chlordantoin, Chlorphenesin, Ciclopirox Olamine, Clotrimazole, Eberconazole, Econazole, Fluconazole, Flutrimazole, Isoconazole, Itraconazole, Ketoconazole, Miconazole, Nifuroxime, Tioconazole, Terconazole, Undecenoic Acid and salts or esters thereof.

Preferred antifungal agents include Clotrimazole, Econazole, Fluconazole, Itraconazole, Ketoconazole, Miconazole, Terconazole and Tioconazole.

Suitable antiprotozoal agents include Acetarsol, Azanidazole, Chloroquine, Metronidazole, Nifuratel, Nimorazole, Omidazole, Propenidazole, Secnidazole, Sineflngin, Tenonitrozole, Temidazole, Timidazole and salts or esters thereof.

Metronidazole, Timidazole and Chloroquine are most preferred antiprotozoal agents.

Suitable antiviral agents include Acyclovir, Brivudine, Cidofovir, Curcumin, Dapirivine, Desciclovir, 1-Docosanol, Edoxudine, Frameyclovir, Fiacitabine, Ibacitabine, Imiquimod, Lamivudine, Penciclovir, Valacyclovir, Valganciclovir and salts or esters thereof. Curcumin, Acyclovir, Famcyclovir, Dapirivine and Valacyclovir are preferred antiviral agents.

The most preferred antimicrobial agents of this invention include, without limitation, Dapirivine, Metronidazole, Acyclovir, Clotrimazole, Fluconazole, Terconazole, Azithromycin, Erythromycin, Doxycycline, Tetracycline, Minocycline, Clindamycin, Famcyclovir, Valacyclovir, Clarithromycin, a prodrug or salt thereof and combinations thereof.

Mixtures of antibacterial agents, mixtures of antifungal agents; mixtures of antiviral agents; mixtures of antiprotozoal agents and mixtures of agents from two or more of these categories are also envisaged by the present invention. In addition, it is also envisaged that the present invention embraces at least one antimicrobial agent (microstatic and/or microcidal agent) with one or more other pharmaceutically active agent.

As used herein, the term "dapivirine" refers to (4-[[4-[(2, 4,6-trimethylphenyl)amino]-2-pyrimidinyl]amino]benzonitrile), a non-nucleoside reverse transcriptase inhibitor. Dapivirine is useful in the prevention and/or treatment of retroviral infection, such as HIV-1 infection. It is a crystalline compound that is white to slightly beige in color, has a melting point of about 220° C. and is virtually insoluble in water. More specifically, the solubility of dapivirine is less than 0.001 mg/gm of water (i.e., less than 1 μg/ml of water). The intravaginal rings of the instant invention may use micronized dapivirine. A composite result (four samples taken of micronized material) showed that 88.15% of the material had a particle size of less than 5 microns (μM).

The antimicrobial compounds contained in the rings of the present invention are further described at least in U.S. Patent Application Publication No. 2006/0166943 and PCT Publication Nos. WO99/50250, WO02/076426 and WO03/094920, the entire contents of each of which are expressly incorporated herein by reference. The antimicrobial compounds contained in the rings of the present invention can be prepared according to art-known procedures. In particular, they are prepared according to the procedures described in EP 1002795, WO 99/50250, WO 99/50256 and WO 00/27828, the entire contents of each of which are incorporated herein by reference.

The antimicrobial compounds contained in the rings of the present invention have microbicidal activity and have the ability to prevent the transmission of HIV. In particular, they can prevent sexual or vaginal transmission of HIV by preventing either the production of infectious viral particles or infection of uninfected cells. If infected cells in sperm can reach the mucosa, the compounds of the present invention can prevent HIV infection of host cells, such as macrophages, lymphocytes, Langerhans and M cells. Thus, these compounds prevent systemic HIV infection of a human being, exhibiting a prophylactic action against HIV.

A. Dapivirine and NNRTIs

In one embodiment of the invention, the antimicrobial agent used in the rings of the invention is dapivirine (see structure, below).

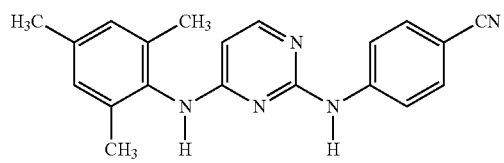 [SMILES: Cc1cc(C)c(Nc2ccnc(Nc3ccc(C#N)cc3)n2)c(C)c1]

Dapivirine was originally developed as an oral antiretroviral compound and was first conceived as an oral therapeutic. Dapivirine has potent activity against wild-type HIV-1 strains and HIV-1 strains harboring different resistance-inducing mutations. (Das et al., *J. Med. Chem.*, 2004; 47 (10):2550-60.) Dapivirine is a white to off-white or slightly yellow powder, free from visible impurities, has a melting point of approximately 220° C., and is virtually insoluble in water. Dapivirine, a substituted DAPY derivate with the chemical name 4-[[4-[(2,4,6-trimethylphenyl)amino]-2-pyrimidinyl]amino]benzonitrile, is a non-nucleoside reverse transcriptase inhibitor (NNRTI).

In another embodiment of the invention, the antimicrobial agent used in the rings of the invention is a NNRTI. Besides dapivirine, other useful NNRTI class compounds include nevirapine, delavirdine, etravirine and efavirenz. NNRTIs bind to the hydrophobic pocket near the active site of the HIV reverse transcriptase (RT) enzyme, blocking DNA polymerization. (See, e.g., Tarby, *Curr. Top. Med. Chem.*, 2004; 4 (10):1045-57, U.S. Patent Application Publication No. US2006/0166943, and PCT Publication No. WO03/094920, the entire contents of each of which are expressly incorporated herein by reference.) This prevents viral replication and, therefore, production of infectious virus. (Borkow et al., *J. Virol.*, 1997; 71 (4):3023-30.)

B. Additional Antimicrobial Compounds

The rings of the present invention may contain compounds having the formula (I), (II) and (III). A compound of formula (I) corresponds to

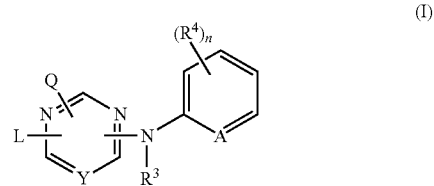

a N-oxide, a pharmaceutically acceptable addition salt or a stereochemically isomeric form thereof, wherein Y is CR5 or N; A is CH, CR4 or N; n is 0, 1, 2, 3 or 4; Q is —NR1R2 or when Y is CR5 then Q may also be hydrogen; R1 and R2 are each independently selected from hydrogen, hydroxy, C1-12alkyl, C1-12alkyloxy, C1-12alkylcarbonyl, C1-12alkyloxycarbonyl, aryl, amino, mono- or di(C1-12alkyl)amino, mono- or di(C1-12alkyl)aminocarbonyl wherein each of the aforementioned C1-12alkyl groups may optionally and each individually be substituted with one or two substituents each independently selected from hydroxy, C1-6alkyloxy, hydroxyC1-6alkyloxy, carboxyl, C1-6alkyloxycarbonyl, cyano, amino, imino, aminocarbonyl, aminocarbonylamino, mono- or di(C1-6alkyl)amino, aryl and Het; or R1 and R2 taken together may form pyrrolidinyl, piperidinyl, morpholinyl, azido or mono- or di(C1-12alkyl) aminoC1-4alkylidene; R3 is hydrogen, aryl, C1-6alkylcarbonyl, C1-6alkyl, C1-6alkyloxycarbonyl, C1-6alkyl substituted with C1-6alkyloxycarbonyl; and each R4 independently is hydroxy, halo, C1-6alkyl, C1-6alkyloxy, cyano, amino-carbonyl, nitro, amino, trihalomethyl, trihalomethyloxy, or when Y is CR5 then R4 may also represent C1-6alkyl substituted with cyano or aminocarbonyl; R5 is hydrogen or C1-4alkyl; L is —X1-R6 or —X2-Alk-R7 wherein R6 and R7 each independently are phenyl or phenyl substituted with one, two, three, four or five substituents each independently selected from halo, hydroxy, C1-6alkyl, C1-6alkyloxy, C1-6alkylcarbonyl, C1-6alkyloxycarbonyl, formyl, cyano, nitro, amino, and trifluoromethyl; or when Y is CR5 then R6 and R7 may also be selected from phenyl substituted with one, two, three, four or five substituents each independently selected from aminocarbonyl, trihalomethyloxy and trihalomethyl; or when Y is N then R6 and R7 may also be selected from indanyl or indolyl, each of said indanyl or indolyl may be substituted with one, two, three, four or five substituents each independently selected from halo, hydroxy, C1-6alkyl, C1-6alkyl-oxy, C1-6alkylcarbonyl, C1-6alkyloxycarbonyl, formyl, cyano, nitro, amino, and trifluoromethyl; when R6 is optionally substituted indanyl or indolyl, it is preferably attached to the remainder of the molecule via the fused phenyl ring. For instance, R6 is suitably 4-, 5-, 6- or 7-indolyl; X1 and X2 are each independently —NR3-, —NH—NH—, —N=N—, —O—, —S—, —S(=O)— or —S(=O)$_2$—; Alk is C1-4alkanediyl; or when Y is CR5 then L may also be selected from C1-10alkyl, C3-10alkenyl, C3-10alkynyl, C3-7cycloalkyl, or C1-10alkyl substituted with one or two substituents independently selected from C3-7cycloalkyl, indanyl, indolyl and phenyl, wherein said phenyl, indanyl and indolyl may be substituted with one, two, three, four or where possible five substituents each independently selected from halo, hydroxy, C1-6alkyl, C1-6alkyloxy, cyano, aminocarbonyl, C1-6alkyloxycarbonyl, formyl, nitro, amino, trihalomethyl, trihalomethyloxy and C1-6alkylcarbonyl; aryl is phenyl or phenyl substituted with one, two, three, four or five substituents each independently selected from halo, C1-6alkyl, C1-6alkyloxy, cyano, nitro and trifluoromethyl; Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic hetero-cyclic radical is selected from pyrrolyl, furanyl, thienyl, pyridyl, pyrimidinyl, pyrazinyl and pyridazinyl wherein each of said aromatic heterocyclic radical may optionally be substituted with hydroxyl.

A compound of formula (II) corresponds to

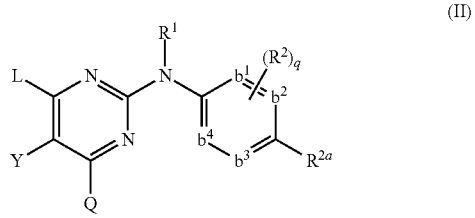

(II)

a N-oxide, a pharmaceutically acceptable addition salt, quaternary amine and the stereochemically isomeric forms thereof, wherein -b1=b2-C(R2a)=b3-b4= represents a bivalent radical of formula —CH=CH—C(R2a)=CH—CH=(b-1); —N=CH—C(R2a)=CH—CH=(b-2); —CH=N—C(R2a)=CH—CH=(b-3); —N=CH—C(R2a)=N—CH=(b-4); —N=CH—C(R2a)=CH—N=(b-5); —CH=N—C(R2a)=N—CH=(b-6); —N=N—C(R2a)=CH—CH=(b-7); q is 0, 1, 2; or where possible q is 3 or 4; R1 is hydrogen, aryl, formyl, C1-6alkylcarbonyl, C1-6alkyl, C1-6alkyloxycarbonyl, C1-6alkyl substituted with formyl, C1-6alkylcarbonyl, C1-6alkyloxycarbonyl; R2a is cyano, aminocarbonyl, mono- or di(methyl)aminocarbonyl, C1-6alkyl substituted with cyano, aminocarbonyl or mono- or di(methyl)aminocarbonyl, C2-6alkenyl substituted with cyano, or C2-6alkynyl substituted with cyano; each R2 independently is hydroxy, halo, C1-6alkyl optionally substituted with cyano or —C(=O)R6, C3-7cycloalkyl, C2-6alkenyl optionally substituted with one or more halogen atoms or cyano, C2-6alkynyl optionally substituted with one or more halogen atoms or cyano, C1-6alkyloxy, C1-6alkyloxycarbonyl, carboxyl, cyano, nitro, amino, mono- or di(C1-6alkyl) amino, polyhalomethyl, polyhalomethyloxy, polyhalomethylthio, —S(=O)pR6, —NH—S(=O)pR6, —C(=O)R6, —NHC(=O)H, —C(=O)NHNH2, —NHC(=O)R6, —C(=NH)R6 or a radical of formula

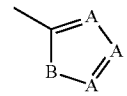

wherein each A independently is N, CH or CR6; B is NH, O, S or NR6; p is 1 or 2; and R6 is methyl, amino, mono- or dimethylamino or polyhalomethyl; L is C1-10alkyl, C2-10alkenyl, C2-10alkynyl, C3-7cycloalkyl, whereby each of said aliphatic group may be substituted with one or two substituents independently selected from C3-7cycloalkyl, indolyl or isoindolyl, each optionally substituted with one, two, three or four substituents each independently selected from halo, C1-6alkyl, hydroxy, C1-6alkyloxy, cyano, aminocarbonyl, nitro, amino, polyhalomethyl, polyhalomethyloxy and C1-6alkylcarbonyl, phenyl, pyridinyl, pyrimidinyl, pyrazinyl or pyridazinyl, wherein each of said aromatic rings may optionally be substituted with one, two, three, four or five substituents each independently selected from the substituents defined in R2; or L is —X—R3 wherein R3 is phenyl, pyridinyl, pyrimidinyl, pyrazinyl or pyridazinyl, wherein each of said aromatic rings may optionally be substituted with one, two, three, four or five substituents each independently selected from the substituents defined in R2; and X is —NR1-, —NH—NH—, —N=N—, —O—, —C(=O)—, —CHOH—, —S—, —S(=O)— or —S(=O) 2-; Q represents hydrogen, C1-6alkyl, halo, polyhaloC1-6alkyl or —NR4R5; and R4 and R5 are each independently selected from hydrogen, hydroxy, C1-12alkyl, C1-12alkyloxy, C1-12alkylcarbonyl, C1-12alkyloxycarbonyl, aryl, amino, mono- or di(C1-12alkyl)amino, mono- or di(C1-12alkyl)aminocarbonyl wherein each of the aforementioned C1-12alkyl groups may optionally and each individually be substituted with one or two substituents each independently selected from hydroxy, C1-6alkyloxy, hydroxyC1-6alkyloxy, carboxyl, C1-6alkyloxycarbonyl, cyano, amino, imino, mono- or di(C1-6alkyl)amino, polyhalomethyl, polyhalomethyloxy, polyhalomethylthio, —S(=O)pR6, —NH—S(=O)pR6, —C(=O)R6, —NHC(=O)H, —C(=O)NHNH2, —NHC(=O)R6, —C(=NH)R6, aryl and Het; or R4 and R5 taken together may form pyrrolidinyl, piperidinyl, morpholinyl, azido or mono- or di(C1-12alkyl) aminoC1-4alkylidene; Y represents hydroxy, halo, C3-7cycloalkyl, C2-6alkenyl optionally substituted with one or more halogen atoms, C2-6alkynyl optionally substituted with one or more halogen atoms, C1-6alkyl optionally substituted with cyano or —C(=O)R6, C1-6alkyloxy, C1-6alkyloxycarbonyl, carboxyl, cyano, nitro, amino, mono- or di(C1-6alkyl)amino, polyhalomethyl, polyhalomethyloxy, polyhalomethylthio, —S(=O)pR6, —NH—S (=O)pR6, —C(=O)R6, —NHC(=O)H, —C(=O)NHNH2, —NHC(=O)R6, —C(=NH)R6 or aryl; aryl is phenyl or phenyl substituted with one, two, three, four or five substituents each independently selected from halo, C1-6alkyl, C3-7cycloalkyl, C1-6alkyloxy, cyano, nitro, polyhaloC1-6alkyl and polyhaloC1-6alkyloxy; Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy; Het is meant to include all the possible isomeric forms of the heterocycles mentioned in the definition of Het, for instance, pyrrolyl also includes 2H-pyrrolyl; the Het radical may be attached to the remainder of the molecule of formula (II) through any ring carbon or heteroatom as appropriate, thus, for example, when the heterocycle is pyridinyl, it may be 2-pyridinyl, 3-pyridinyl or 4-pyridinyl.

A compound of formula (III) corresponds to

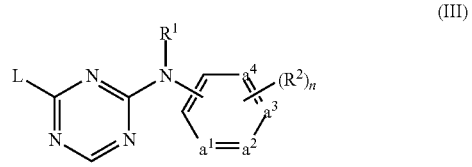

(III)

a N-oxide, a pharmaceutically acceptable addition salt, quaternary amine and the stereochemically isomeric forms thereof, wherein -a1=a2-a3=a4- represents a bivalent radical of formula —CH=CH—CH=CH-(a-1); —N=CH—CH=CH-(a-2); —N=CH—N=CH-(a-3); —N=CH—CH=N-(a-4); —N=N—CH=CH-(a-5); n is 0, 1, 2, 3 or 4; and in case -a1=a2-a3=a4- is (a-1), then n may also be 5; R1 is hydrogen, aryl, formyl, C1-4alkylcarbonyl, C1-6alkyl, C1-6alkyloxycarbonyl, C1-6alkyl substituted with formyl, C1-6alkylcarbonyl, C1-6alkyloxycarbonyl; and each R2 independently is hydroxy, halo, C1-6alkyl optionally substituted with cyano or —C(=O)R4, C3-7cycloalkyl, C2-6alkenyl optionally substituted with one or more halogen atoms or cyano, C2-6alkynyl optionally substituted with one or more halogen atoms or cyano, C1-6alkyloxy, C1-6alkyloxycarbonyl, carboxyl, cyano, nitro, amino, mono- or di(C1-6alkyl)amino, polyhalomethyl, polyhalomethyloxy, polyhalomethylthio, —S(=O)pR4, —NH—S(=O)pR4, —C(=O)R4, —NHC(=O)H, —C(=O)NHNH2, —NHC(=O)R4, —C(=NH)R4 or a radical of formula

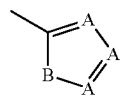

wherein each A independently is N, CH or CR4; B is NH, O, S or NR4; p is 1 or 2; and R4 is methyl, amino, mono- or dimethylamino or polyhalomethyl; L is C1-10alkyl, C2-10alkenyl, C2-10alkynyl, C3-7cycloalkyl, whereby each of said aliphatic group may be substituted with one or two substituents independently selected from C3-7cycloalkyl, indolyl or isoindolyl, each optionally substituted with one, two, three or four substituents each independently selected from halo, C1-6alkyl, hydroxy, C1-6alkyloxy, cyano, aminocarbonyl, nitro, amino, polyhalomethyl, polyhalomethyloxy and C1-6alkylcarbonyl, phenyl, pyridinyl, pyrimidinyl, pyrazinyl or pyridazinyl, wherein each of said aromatic rings may optionally be substituted with one, two, three, four or five substituents each independently selected from the substituents defined in R2; or L is —X—R3 wherein R3 is phenyl, pyridinyl, pyrimidinyl, pyrazinyl or pyridazinyl, wherein each of said aromatic rings may optionally be substituted with one, two, three, four or five substituents each independently selected from the substituents defined in R2; and X is —NR1-, —NH—NH—, —N=N—, —O—, —C(=O)—, —CHOH—, —S—, —S(=O)— or —S(=O)2—; aryl is phenyl or phenyl substituted with one, two, three, four or five substituents each independently selected from halo, C1-6alkyl, C3-7cycloalkyl, C1-6alkyloxy, cyano, nitro, polyhaloC1-6alkyl and polyhaloC1-6alkyloxy; with the proviso that compounds of formula (III) wherein L is C1-3alkyl; R1 is selected from hydrogen, ethyl and methyl; -a1=a2-a3=a4- represents a bivalent radical of formula (a-1); n is 0 or 1 and R2 is selected from fluoro, chloro, methyl, trifluoromethyl, ethyloxy and nitro; or L is —X—R3, X is —NH—; R1 is hydrogen; -a1=a2-a3=a4- represents a bivalent radical of formula (a-1); n is 0 or 1 and R2 is selected from chloro, methyl, methyloxy, cyano, amino and nitro and R3 is phenyl, optionally substituted with one substituent selected from chloro, methyl, methyloxy, cyano, amino and nitro; and the compounds N,N'-dipyridinyl-(1,3,5)-triazine-2,4-diamine; (4-chloro-phenyl)-(4(1-(4-isobutyl-phenyl)-ethyl)- (1,3,5)triazin-2-yl)-amine are not included.

The rings of the present invention may contain a compound of formula (I), (II) or (III) wherein Y in the compound of formula (II) represents hydroxy, halo, C3-7cycloalkyl, C2-6alkenyl optionally substituted with one or more halogen atoms, C2-6alkynyl optionally substituted with one or more halogen atoms, C1-6alkyl substituted with cyano or —C(=O)R6, C1-6alkyloxy, C1-6alkyloxycarbonyl, carboxyl, cyano, nitro, amino, mono- or di(C1-6alkyl)amino, polyhalomethyl, polyhalomethyloxy, polyhalomethylthio, —S(=O)pR6, —NH—S(=O)pR6, —C(=O)R6, —NHC(=O)H, —C(=O)NHNH2, —NHC(=O)R6, —C(=NH)R6 or aryl.

In another embodiment, the rings of the present invention may contain compounds of the formula (IV). A compound of formula (IV) corresponds to

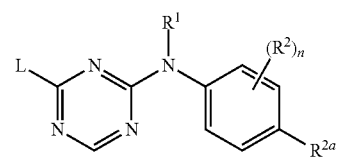

a N-oxide, a pharmaceutically acceptable addition salt, quaternary amine and the stereochemically isomeric forms thereof, wherein n is 0, 1, 2, 3 or 4; R1 is hydrogen, aryl, formyl, C1-6alkylcarbonyl, C1-6alkyl, C1-6alkyloxycarbonyl, C1-6alkyl substituted with formyl, C1-6alkylcarbonyl, C1-6alkyloxycarbonyl; and R2a is cyano; aminocarbonyl; mono- or dimethylaminocarbonyl; C1-6alkyl optionally substituted with cyano, aminocarbonyl, or mono- or dimethylaminocarbonyl; C2-6alkenyl substituted with cyano; and C2-6alkynyl substituted with cyano; each R2 independently is hydroxy, halo, C1-6alkyl optionally substituted with cyano or —C(=O)R4, C3-7cycloalkyl, C2-6alkenyl optionally substituted with one or more halogen atoms or cyano, C2-6alkynyl optionally substituted with one or more halogen atoms or cyano, C1-6alkyloxy, C1-6alkyloxycarbonyl, carboxyl, cyano, nitro, amino, mono- or di(C1-6alkyl)amino, polyhalomethyl, polyhalomethyloxy, polyhalomethylthio, —S(=O)pR4, —NH—S(=O)pR4, —C(=O)R4, —NHC(=O)H, —C(=O)NHNH2, —NHC(=O)R4, —C(=NH)R4 or a radical of formula

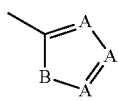

wherein each A independently is N, CH or CR4; B is NH, O, S or NR4, p is 1 or 2; and R4 is methyl, amino, mono- or dimethylamino or polyhalomethyl; L is C1-10alkyl, C2-10alkenyl, C2-10alkynyl, C3-7cycloalkyl, each of said aliphatic group substituted with phenyl, which may optionally be substituted with one, two, three, four or five substituents each independently selected from the substituents defined in R2; or L is —X—R3 wherein R3 is phenyl, optionally substituted with one, two, three, four or five substituents each independently selected from the substituents defined in R2; and X is —NR1-, —NH—NH—, —N=N—, —O—, —C(=O)—, —CHOH—, —S—, —S(=O)— or —S(=O)2-; aryl is phenyl or phenyl substituted with one, two, three, four or five substituents each independently selected from halo, C1-6alkyl, C3-7cycloalkyl, C1-6alkyloxy, cyano, nitro, polyhaloC1-6alkyl and polyhaloC1-6alkyloxy; with the proviso that the compound 2,4-di-p-cyanoanilino-1,3,5-triazine is not included.

As used in the foregoing definitions and hereinafter halo defines fluoro, chloro, bromo and iodo; polyhalomethyl as a group or part of a group is defined as mono- or polyhalo-substituted methyl, in particular methyl with one or more fluoro atoms, for example, difluoromethyl or trifluoromethyl; polyhaloC1-6alkyl as a group or part of a group is defined as mono- or polyhalosubstituted C1-6alkyl, for example, the groups defined in halomethyl, 1,1-difluoroethyl and the like; in case more than one halogen atoms are attached to an alkyl group within the definition of polyhalomethyl or polyhaloC1-6alkyl, they may be the same or different; C1-4alkyl as a group or part of a group encompasses the straight and branched chained saturated hydrocarbon radicals having from 1 to 4 carbon atoms such as, for example, methyl, ethyl, propyl, butyl and the like; C1-6alkyl as a group or part of a group encompasses the straight and branched chained saturated hydrocarbon radicals as defined in C1-4alkyl as well as the higher homologues thereof containing 5 or 6 carbon atoms such as, for example pentyl or hexyl; C1-10alkyl as a group or part of a group encompasses the straight and branched chained saturated hydrocarbon radicals as defined in C1-6alkyl as well as the higher homologues thereof containing 7 to 10 carbon atoms such as, for example, heptyl, octyl, nonyl or decyl; C1-12alkyl as a group or part of a group encompasses the straight and branched chained saturated hydrocarbon radicals as defined in C1-10alkyl as well as the higher homologues thereof containing 11 or 12 carbon atoms such as, for example, undecyl, dodecyl and the like; C1-4alkylidene as a group or part of a group defines bivalent straight and branched chained hydrocarbons having from 1 to 4 carbon atoms such as, for example, methylene, ethylidene, propylidene, butylidene and the like; C1-4alkanediyl as a group or part of a group encompasses those radicals defined under C1-4alkylidene as well as other bivalent straight and branched chained hydrocarbons having from 1 to 4 carbon atoms such as, for example, 1,2-ethanediyl, 1,3-propanediyl, 1,4-butanediyl and the like; C3-7cycloalkyl as a group or part of a group is generic to cyclopropyl, cyclobutyl, cyclopentyl, cyclohexyl and cycloheptyl; C3-10alkenyl as a group or part of a group defines straight and branch chained hydrocarbon radicals containing one double bond and having from 3 to 10 carbon atoms such as, for example, 2-propenyl, 2-butenyl, 2-pentenyl, 3-pentenyl, 3-methyl-2-butenyl, 3-hexenyl, 3-heptenyl, 2-octenyl, 2-nonenyl, 2-decenyl and the like, whereby the carbon atom attached to the pyrimidine ring is preferably an aliphatic carbon atom; C3-10alkynyl as a group or part of a group defines straight and branch chained hydrocarbon radicals containing one triple bond and having from 3 to 10 carbon atoms such as, for example, 2-propynyl, 2-butynyl, 2-pentynyl, 3-pentynyl, 3-methyl-2-butynyl, 3-hexynyl, 3-heptynyl, 2-octynyl, 2-nonynyl, 2-decynyl and the like, whereby the carbon atom attached to the pyrimidine ring is preferably an aliphatic carbon atom; C2-6alkenyl defines straight and branched chain hydrocarbon radicals having from 2 to 6 carbon atoms containing a double bond such as ethenyl, propenyl, butenyl, pentenyl, hexenyl and the like; C2-10alkenyl defines straight and branched chain hydrocarbon radicals having from 2 to 10 carbon atoms containing a double bond such as the groups defined for C2-6alkenyl and heptenyl, octenyl, nonenyl, decenyl and the like; C2-6alkynyl defines straight and branched chain hydrocarbon radicals having from 2 to 6 carbon atoms containing a triple bond such as ethynyl, propynyl, butynyl, pentynyl, hexynyl and the like; C2-10alkynyl defines straight and branched chain hydrocarbon radicals having from 2 to 10 carbon atoms containing a triple bond such as the groups defined for C2-6alkynyl and heptynyl, octynyl, nonynyl, decynyl and the like; C1-3alkyl as a group or part of a group encompasses the straight and branched chain saturated hydro-carbon radicals having from 1 to 3 carbon atoms such as, methyl, ethyl and propyl; C4-10alkyl encompasses the straight and branched chain saturated hydrocarbon radicals as defined above, having from 4 to 10 carbon atoms. The term C1-6alkyloxy defines straight or branched chain saturated hydrocarbon radicals such as methoxy, ethoxy, propyloxy, butyloxy, pentyloxy, hexyloxy, 1-methylethyloxy, 2-methylpropyloxy, 2-methylbutyloxy and the like; C3-6cycloalkyloxy is generic to cyclopropyloxy, cyclobutyloxy, cyclopentyloxy and cyclohexyloxy.

As used herein, the term (=O) forms a carbonyl moiety when attached to a carbon atom, a sulfoxide group when attached once to a sulfur atom, and a sulfonyl group when attached twice to a sulfur atom.

When any variable (e.g., aryl, etc.) occurs more than one time in any constituent, each definition is independent.

Lines drawn into ring systems from substituents indicate that the bond may be attached to any of the suitable ring atoms. For instance for compounds of formula (I), R4 can be attached to any available carbon atom of the phenyl or pyridyl ring.

The rings of the present invention may also comprise salts of the compounds described herein. Pharmaceutically acceptable addition salts as mentioned herein are meant to comprise the microbicidal active non-toxic addition salt forms which the compounds contained in the rings of the present invention are able to form. The latter can conveniently be obtained by treating the base form with such appropriate acids as inorganic acids, for example, hydrohalic acids, e.g., hydrochloric or hydrobromic acid and the like; sulfuric acid; nitric acid; phosphoric acid and the like; or organic acids, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluene-sulfonic, cyclamic, salicylic, p-aminosalicylic, pamoic and the like acids. Conversely the salt form can be converted by treatment with alkali into the free base form.

The pharmaceutically acceptable addition salts as mentioned hereinabove are also meant to comprise the microbicidal active non-toxic base forms, in particular, metal or amine addition salt forms which the compounds of the present invention are able to form. Said salts can conveniently be obtained by treating the compounds of the present invention containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely said salt forms can be converted by treatment with acid into the free acid form.

The term addition salts comprises as well the hydrates and the solvent addition forms which the compounds of the present invention are able to form. Examples of such forms are e.g., hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g., methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds wherein one or several tertiary nitrogen atoms are oxidized to the so-called N-oxide.

The term stereochemically isomeric forms of the compounds of the present invention, their N-oxides, addition salts, quaternary amines, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms that said compound may possess. Said mixture may contain all diastereomers and/or enantiomers of the basic molecular structure of said compound. All stereochemically isomeric forms of the compounds both in pure form or in admixture with each other are intended to be embraced within the scope of the present invention.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Some of the present compounds may also exist in their tautomeric forms. Such forms although not explicitly indicated in the above formula are intended to be included within the scope of the present invention.

Whenever used hereinafter, the term "compounds", used in the rings of the present invention is meant to include any subgroup of the compounds described herein, also the N-oxide forms, the pharmaceutically acceptable addition salts, the quaternary amines and all stereochemically isomeric forms. Of special interest are those compounds which are stereochemically pure.

Whenever substituents can be selected each independently from a list of numerous definitions, such as for example for R6 and R7, all possible combinations are intended which are chemically possible and which lead to chemically stable molecules.

Suitable compounds of formula (I) are those wherein Y is CR5 or N; A is CH, CR4 or N; n is 0, 1, 2, 3 or 4; Q is —NR1R2; R1 and R2 are each independently selected from hydrogen, hydroxy, C1-12alkyl, C1-12alkyloxy, C1-12alkylcarbonyl, C1-12alkyloxy-carbonyl, aryl, amino, mono- or di(C1-12alkyl)amino, mono- or di(C1-12alkyl)amino-carbonyl wherein each of the aforementioned C1-12alkyl groups may optionally and each individually be substituted with one or two substituents each independently selected from hydroxy, C1-6alkyloxy, hydroxyC1-6alkyloxy, carboxyl, C1-6alkyloxy-carbonyl, cyano, amino, imino, aminocarbonyl, aminocarbonylamino, mono- or di(C1-6alkyl)amino, aryl and Het; or R1 and R2 taken together may form pyrrolidinyl, piperidinyl, morpholinyl, azido or mono- or di(C1-12alkyl)aminoC1-4alkylidene; R3 is hydrogen, aryl, C1-6alkylcarbonyl, C1-6alkyl, C1-6alkyloxycarbonyl, C1-6alkyl substituted with C1-6alkyloxycarbonyl; each R4 independently is hydroxy, halo, C1-6alkyl, C1-6alkyloxy, cyano, aminocarbonyl, nitro, amino, trihalomethyl, trihalomethyloxy; R5 is hydrogen or C1-4alkyl; L is —X1-R6 or —X2-Alk-R7 wherein R6 and R7 each independently are phenyl or phenyl substituted with one, two, three, four or five substituents each independently selected from halo, hydroxy, C1-6alkyl, C1-6alkyloxy, C1-6alkylcarbonyl, C1-6alkyloxycarbonyl, formyl, cyano, nitro, amino, and trifluoromethyl, X1 and X2 are each independently —NR3-, —NH—NH—, —N=N—, —O—, —S—, —S(=O)— or —S(=O)$_2$—, and Alk is C1-4alkanediyl; aryl is phenyl or phenyl substituted with one, two, three, four or five substituents each independently selected from halo, C1-6alkyl, C1-6alkyloxy, cyano, nitro and trifluoromethyl; Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridyl, pyrimidinyl, pyrazinyl and pyridazinyl wherein each of said aromatic heterocyclic radical may optionally be substituted with hydroxy.

Most preferred compounds of formula (I) are:
4-[[4-amino-6-[(2,6-dichlorophenyl)methyl]-2-pyrimidinyl] amino]benzonitrile; 6-[(2,6-dichlorophenyl)methyl]-N2-(4-fluorophenyl)-2,4-pyrimidinediamine; 4-[[4-[(2,4-dichlorophenyl)methyl]-6-[(4-hydroxybutyl)amino]-2-pyrimidinyl]amino]-benzonitrile; 4-[[4-[(2,6-dichlorophenyl)methyl]-6-[(3-hydroxypropyl)amino]-2-pyrimidinyl]-amino]benzonitrile; N-[2-[(4-cyanophenyl)amino]-6-[(2,6-dichlorophenyl)methyl]-4-pyrimidinyl]-1-acetamide; N-[2-[(4-cyanophenyl)amino]-6-[(2,6-dichlorophenyl)methyl]-4-pyrimidinyl]-1-butanamide; 4-[[2-amino-6-(2,6-dichlorophenoxy)-4-pyrimidinyl] amino]benzonitrile; 4-[[4-[(2,6-dichlorophenyl)methyl]-6-[(2-hydroxy-2-phenylethyl)amino]-2-pyrimidinyl] amino]benzonitrile; 4-[[4-[(2,6-dichlorophenyl)methyl]-6-[[3-(2-oxo-1-pyrrolidinyl)propyl]amino]-2-pyrimidinyl]amino]benzonitrile; 4-[[4-[(2,6-dichlorophenyl)methyl]-6-[[2-(2-hydroxyethoxy)ethyl] amino]-2-pyrimidinyl]amino]benzontrile monohydrochloride; 4-[[4-[(2,6-dichlorophenyl)methyl]-6-[(2,3-dihydroxypropyl)amino]-2-pyrimidinyl]-amino benzonitrile; 4-[[4-[(2,6-dichlorophenyl)methyl]-6-(hydroxyamino)-2-pyrimidinyl]amino]-benzonitrile; 4-[[4-[(2-cyanoethyl)amino]-6-[(2,6-dichlorophenyl)methyl]-2-pyrimidinyl]-amino]-benzonitrile; 4-[[4-[(2,6-dichlorophenyl)methyl]-6-[[2-(1-pyrrolidinyl)ethyl] amino]-2-pyrimidinyl]-amino]benzonitrile; 4-[[4-amino-6-[(2,6-dichlorophenyl)methyl]-5-methyl-2-pyrimidinyl] amino]-benzonitrile; N2-(4-bromophenyl)-6-[(2,6-dichlorophenyl)methyl]-5-methyl-2,4-pyrimidinediamine; 4-[[4-[(2,4,6-trimethylphenyl)amino]-2-pyrimidinyl]amino]benzonitrile; 4-[[2-[(2,4,6-trimethylphenyl)amino]-4-pyrimidinyl]amino] benzonitrile; 4-[[4-[(2,6-dimethylphenyl)amino]-2-pyrimidinyl]amino]benzonitrile; 4-[[4-(2,4,6-trimethylphenoxy)-2-pyrimidinyl]amino]benzonitrile; 4-[[4-[(2,6-dichlorophenyl)thio]-2-pyrimidinyl]amino] benzonitrile; 4-[[4-[[2,6-dibromo-4-(1-methylethyl)phenyl]amino]-2-pyrimidinyl]-amino]benzonitrile; 4-[[4-[[2,6-dichloro-4-(trifluoromethyl)phenyl]amino]-2-pyrimidinyl]amino]-benzonitrile; 4-[[4-[(2,4-dichloro-6-methylphenyl)amino]-2-pyrimidinyl]amino]benzonitrile; 4-[[2-[(cyanophenyl)amino]-4-pyrimidinyl]amino]-3,5-dimethylbenzonitrile; 4-[[4-[(2,4-dibromo-6-fluorophenyl)amino]-2-pyrimidinyl]amino]benzonitrile; 4-[[4-amino-6-[(2,6-dichlorophenyl)methyl]-5-methyl-2-pyrimidinyl]amino]-benzeneacetonitrile; 4-[[4-[methyl(2,4,6-trimethylphenyl)amino]-2-pyrimidinyl]amino] benzonitrile; 4-[[4-[(2,4,6-trichlorophenyl)amino]-2-pyrimidinyl]amino]benzonitrile; 4-[[4-[(2,4,6-trimethylphenyl)thio]-2-pyrimidinyl]amino]benzonitrile; 4-[[4-[(2,4,6-trimethylphenyl)amino-2-pyrimidinyl] amino]benzonitrile; 4-[[4-amino-6-[(2,4,6-trimethylphenyl)amino]-2-pyrimidinyl]amino]benzonitrile; 4-[[2-amino-6-[(2,4,6-trimethylphenyl)amino]-4-pyrimidinyl] amino]benzonitrile; 4-[[4-(2-bromo-4-chloro-6-methylphenoxy)-2-pyrimidinyl]amino]benzonitrile-; 4-[[4-[(4-chloro-2,6-dimethylphenyl)amino]-2-pyrimidinyl]amino]benzonitrile; 3,5-dichloro-4-[[2-[(4-cyanophenyl)amino]-4-pyrimidinyl]amino]benzonitrile; 4-[[4-[[2,6-dichloro-4-(trifluoromethoxy)phenyl]amino]-2-pyrimidinyl]amino]-benzonitrile; 4-[[4-[(2,4-dibromo-3,6-dichlorophenyl)amino]-2-pyrimidinyl]amino] benzonitrile; 4-[[4-[(2,6-dibromo-4-propylphenyl) amino]-2-pyrimidinyl]amino]benzonitrile; 4-[[4-[(2,4,6-trimethylphenyl)amino]-2-pyrimidinyl]amino] benzamide; 4-[[4-[(4-(1,1-dimethylethyl)-2,6-dimethylphenyl)amino]-2-pyrimidinyl]amino]-benzonitrile; 4-[[2-[(4-cyanophenyl)amino]-4-pyrimidinyl]oxy]-3,5-dimethylbenzonitrile; 4-[[4-[(4-chloro-2,6-dimethylphenyl)amino]-5-methyl-2-pyrimidinyl-]amino]-benzonitrile; 4-[[2-[(4-cyanophenyl)amino]-5-methyl-4-pyrimidinyl]amino-3,5-dimethylbenzonitrile; 4-[[4-[[4-(1,1-dimethylethyl)-2,6-dimethylphenyl]amino]-5-methyl-2-pyrimidinyl-amino] benzonitrile; 4-[[4-[(4-bromo-2,6-dimethylphenyl) amino]-5-methyl-2-pyrimidinyl]amino]-benzonitrile; 4-[[5-methyl-4-[(2,4,6-trimethylphenyl)thio]-2-pyrimidinyl]amino]benzonitrile; 4-[[4-[(2,6-dibromo-4-propylphenyl)amino]-5-methyl-2-pyrimidinyl]amino]-benzonitrile; 4-[[4-[(2,4,6-trimethylphenyl)amino]-2-pyrimidinyl]amino]benzamide, N3-oxide; N2-(4-chlorophenyl)-N4-(2,4,6-trimethylphenyl)-2,4-pyrimidinediamine; 4-[[4-[[2,6-dibromo-4-(1-methylethyl)phenyl]amino]-5-methyl-2-pyrimidinyl] amino]-benzonitrile; 4-[[2-[(4-cyanophenyl)amino]-5-methyl-4-pyrimidinyl]amino]-3,5-dimethylbenzonitrile; 4-[[4-[(phenylmethyl)amino]-2-pyrimidinyl]amino]benzonitrile; 4-[[4-amino-6-(2,6-dimethylphenoxy)-1,3,5-triazin-2-yl]amino]benzonitrile; 4-[[4-amino-6-[(2-chloro-6-methylphenyl)amino]-1,3,5-triazin-2-yl]amino] benzonitrile; 4-[[4-amino-6-[(2,4,6-trimethylphenyl) amino]-1,3,5-triazin-2-yl]amino]benzonitrile; 4-[[4-(hydroxyamino)-6-[(2,4,6-trimethylphenyl)amino]-1,3,5-triazin-2-yl]-amino]-benzonitrile; 4-[[4-amino-6-[(2-ethyl-6-methylphenyl)amino]-1,3,5-triazin-2-yl]amino] benzonitrile; 4-[[4-amino-6-[(2,6-dichlorophenyl)thio]-1,3,5-triazin-2-yl]amino]benzonitrile; 4-[[4-(hydroxyamino)-6-[(2,4,6-trichlorophenyl)amino]-1,3,5-triazin-2-yl]-amino]-benzonitrile; 4-[[4-amino-6-(2,4,6-trimethylphenoxy)-1,3,5-triazin-2-yl]amino]benzonitrile; 4-[[4-(hydroxyamino)-6-(2,4,6-trimethylphenoxy)-1,3,5-triazin-2-yl]amino]-1-benzonitrile; 4-[[4-amino-6-[(2,4-dichloro-6-methylphenyl)amino]-1,3,5-triazin-2-yl] amino]-benzonitrile; 4-[[4-[(2,4-dichloro-6-methylphenyl)amino]-6-(hydroxyamino)-1,3,5-triazin-2-yl]-amino]benzonitrile; 4-[[4-(hydroxyamino)-6-(2,4,6-trichlorophenoxy)-1,3,5-triazin-2-yl]amino]-benzonitrile trifluoroacetate (1:1); 4-[[4-(4-acetyl-2,6-dimethylphenoxy)-6-amino-1,3,5-triazin-2-yl]amino]benzonitrile; 4-[[4-amino-6-(2,4,6-tribromophenoxy)-1,3,5-triazin-2-yl]amino]benzonitrile; 4-[[4-amino-6-(4-nitro-2,6-dimethylphenoxy)-1,3,5-triazin-2-yl]amino]benzonitrile; 4-[[4-amino-6-(2,6-dibromo-4-methylphenoxy)-1,3,5-triazin-2-yl]amino]benzonitrile; 4-[[4-amino-6-(4-formyl-2,6-dimethylphenoxy)-1,3,5-triazin-2-yl]amino]benzonitrile; 4-[[4-amino-6-[(2,4-dichlorophenyl)thio]-1,3,5-triazin-2-yl]amino]benzonitrile; 4-[[4-[(5-acetyl-2,3-dihydro-7-methyl-1H-inden-4-yl)oxy]-6-amino-1,3,5-triazin-2-yl]-amino]benzonitrile; 4-[[4-amino-6-[(4-bromo-2-chloro-6-methylphenyl)amino]-1,3,5-triazin-2-yl]amino]-benzonitrile; 4-[[4-amino-6-[(2-chloro-4,6-dimethylphenyl)amino]-1,3,5-triazin-2-yl]amino]-benzonitrile; 4-[[4-amino-6-[[2,4-dichloro-6-(trifluoromethyl)phenyl]amino]-1,3,5-triazin-2-yl]-amino]benzonitrile; 4-[[4-amino-6-[methyl(2,4,6-trimethylphenyl)amino]-1,3,5-triazin-2-yl]amino]-benzonitrile; 4-[[4-amino-6-[(2,6-dibromo-4-methylphenyl)amino]-1,3,5-triazin-2-yl]amino]-benzonitrile; 4-[[4-amino-6-[[2,6-dibromo-4-(1-methylethyl)phenyl]amino]-1,3,5-triazin-2-yl]-amino]

benzonitrile; the N-oxides, the pharmaceutically acceptable addition salts and the stereochemically isomeric forms thereof.

Suitable compounds of formula (II) are those wherein one or more of the following restrictions apply: -b1=b2-C(R2a)=b3-b4= is a radical of formula (b-1); q is 0; R2a is cyano or —C(=O)NH2, preferably R2a is cyano; Y is cyano, —C(=O)NH2 or a halogen, preferably a halogen; Q is hydrogen or —NR4R5 wherein R4 and R5 are preferably hydrogen; L is —X—R3 wherein X is preferably —NR1-, —O— or —S—, most preferably X is —NH—, and R3 is substituted phenyl with C1-6alkyl, halogen and cyano as preferred substituents.

Another interesting group of compounds of formula (II) are those compounds wherein L is —X—R3 wherein R3 is 2,4,6-trisubstituted phenyl, each substituent independently selected from chloro, bromo, fluoro, cyano or C1-4alkyl.

Also interesting are those compounds of formula (II) wherein Y is chloro or bromo and Q is hydrogen or amino.

Particular compounds are those compounds of formula (II) wherein the moiety in the 2 position of the pyrimidine ring is a 4-cyano-anilino group.

Preferred compounds are those compounds of formula (II) wherein the moiety in the 2 position of the pyrimidine ring is a 4-cyano-anilino group, L is —X—R3 wherein R3 is a 2,4,6-trisubstituted phenyl, Y is a halogen and Q is hydrogen or NH2.

Most preferred compounds of formula (II) are: 4-[[4-amino-5-chloro-6-[(2,4,6-trimethylphenyl)amino]-2-pyrimidinyl]amino]-benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]-amino]-benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]-benzonitrile; and 4-[[4-amino-5-bromo-6-(4-cyano-2,6-dimethylphenyloxy)-2-pyrimidinyl]amino]-benzonitrile; the N-oxides, the pharmaceutically acceptable addition salts, quaternary amines and the stereochemically isomeric forms thereof.

An interesting group of compounds are those compounds of formula (III) wherein one or more of the following conditions are met: n is 1; -a1=a2-a3=a4- represents a bivalent radical of formula (a-1); R1 is hydrogen or C1-4alkyl; R2 is cyano; aminocarbonyl; mono- or di(methyl)aminocarbonyl; C1-6alkyl substituted with cyano, aminocarbonyl or mono- or di(methyl)aminocarbonyl; and more in particular, R2 is on the 4 position relative to the —NR1- moiety; L is —X—R3 wherein X is preferably —NR1-, —O— or —S—, most preferably X is —NH—, and R3 is substituted phenyl with C1-6alkyl, halogen and cyano as preferred substituents.

Preferred compounds are those compounds of formula (III) wherein L is —X—R3 wherein R3 is a disubstituted phenyl group or a trisubstituted phenyl group, each substituent independently selected from chloro, bromo, fluoro, cyano or C1-4alkyl.

Most preferred compound of formula (III) is 4-[[4-[(2,4,6-trimethylphenyl)amino]-1,3,5-triazin-2-yl]amino]benzonitrile.

Particular compounds of the present invention include 4-[[4-amino-5-bromo-6-(4-cyano-2,6-dimethylphenyloxy)-2-pyrimidinyl]amino]benzonitrile (compound A) and 4-[[4-[(2,4,6-trimethylphenyl)amino]-2-pyrimidinyl]amino]benzonitrile (compound B), their N-oxides, pharmaceutically acceptable salts and stereoisomers thereof.

III. Methods for Preventing/Treating HIV

The present invention also provides methods of preventing and/or treating HIV. In one aspect, the present invention provides methods of blocking DNA polymerization by an HIV reverse transcriptase enzyme in a female human, comprising the step of inserting an intravaginal ring of the invention into the vagina of the female human. In another aspect, the present invention provides methods of preventing HIV infection in a female human, comprising the step of inserting an intravaginal ring of the invention into the vagina of the female human. In yet another aspect, the invention provides methods of treating HIV infection in a female human, comprising the step of inserting an intravaginal ring of the invention into the vagina of the female human.

The ring that is inserted into a human may contain a prophylactically effective amount or a therapeutically effective amount of an antimicrobial compound, e.g., dapivirine.

As used herein, the term "prophylactically effective amount" refers to the amount of antimicrobial compound effective to prevent development of disease in the subject. In one embodiment of the invention, the disease is HIV. In a preferred embodiment of the invention, a prophylactically effective amount is achieved when between about 1 mg and about 3 mg of the antimicrobial compound is released in vitro during an initial 24 hour period of release. In one embodiment of the invention, a prophylactically effective amount is achieved when between about 100 micrograms to about 500 micrograms of the antimicrobial compound is released in vitro per day after the initial 7 day period of release. In one embodiment of the invention, a prophylactically effective amount is achieved when between about 200 micrograms to about 400 micrograms of the antimicrobial compound is released in vitro per day after the initial 7 day period of release. In another embodiment of the invention, a prophylactically effective amount is achieved when between about 250 micrograms to about 350 micrograms of the antimicrobial compound is released in vitro per day after the initial 7 day period of release. In another embodiment of the invention, a prophylactically effective amount is achieved when between about 350 micrograms to about 400 micrograms of the antimicrobial compound is released in vitro per day after the initial 7 day period of release. In one embodiment, a prophylactically effective amount is achieved when about 50 micrograms, about 100 micrograms, about 125 micrograms, about 150 micrograms, about 175 micrograms, about 200 micrograms, about 225 micrograms, about 250 micrograms, about 275 micrograms, about 300 micrograms, about 325 micrograms, about 350 micrograms, about 375 micrograms, about 400 micrograms, about 450 micrograms, about 475 micrograms, about 500 micrograms, about 550 micrograms, about 600 micrograms, about 650 micrograms, about 700 micrograms, about 750 micrograms, about 800 micrograms, about 850 micrograms, about 900 micrograms about 950 micrograms, about 1 mg, less than 1 mg or more than 1 mg of the antimicrobial compound is released in vitro per day after the initial 7 day period of release.

In another embodiment, a prophylactically effective amount is achieved when between about 5 micrograms and about 300 micrograms of the antimicrobial compound is released in vivo per gram of vaginal fluid each day for 24 days after an initial 3 day period of use. In another embodiment, a prophylactically effective amount is achieved when between about 10 micrograms and about 100 micrograms of the antimicrobial compound is released in vivo per gram of vaginal fluid each day for 24 days after an initial 3 day period of use. In another embodiment, a prophylactically effective amount is achieved when between about 20 micrograms and about 80 micrograms of the antimicrobial compound is released in vivo per gram of vaginal fluid each day for 24 days after an initial 3 day period of use. In yet another embodiment, a prophylactically effective amount is achieved when about 5 micrograms, about 10 micrograms, about 25 micrograms, about 50 micrograms, about 75 micrograms, about 100 micrograms, about 125 micrograms, about 150 micrograms, about 175 micrograms, about 200 micrograms, about 225 micrograms, about 250 micrograms, about 275 micrograms, about 300 micrograms, about 350 micrograms, about 400 micrograms, about 450 micrograms, about 500 micrograms, or about 600 micrograms of the antimicrobial compound is released in vivo per gram of vaginal fluid each day for 24 days after an initial 3 day period of use.

Values and ranges included and/or intermediate within the ranges set forth herein are also intended to be within the scope of the present disclosure. Ranges having values recited herein as an upper or lower limit are also intended to be within the scope of the present disclosure.

As used herein, the term "therapeutically effective amount" refers to the amount of antimicrobial compound effective to treat disease in the subject. In one embodiment of the invention, the disease is HIV. In a preferred embodiment of the invention, a therapeutically effective amount is achieved when between about 1 mg and about 3 mg of the antimicrobial compound is released in vitro during an initial 24 hour period of release. In one embodiment of the invention, a therapeutically effective amount is achieved when between about 100 micrograms to about 500 micrograms of the antimicrobial compound is released in vitro per day after the initial 7 day period of release. In one embodiment of the invention, a therapeutically effective amount is achieved when between about 200 micrograms to about 400 micrograms of the antimicrobial compound is released in vitro per day after the initial 7 day period of release. In another embodiment of the invention, a therapeutically effective amount is achieved when between about 250 micrograms to about 350 micrograms of the antimicrobial compound is released in vitro per day after the initial 7 day period of release. In another embodiment of the invention, a therapeutically effective amount is achieved when between about micrograms to about 400 micrograms of the antimicrobial compound is released in vitro per day after the initial 7 day period of release. In one embodiment, a therapeutically effective amount is achieved when about 100 micrograms, about 125 micrograms, about 150 micrograms, about 175 micrograms, about 200 micrograms, about 225 micrograms, about 250 micrograms, about 275 micrograms, about 300 micrograms, about 325 micrograms, about 350 micrograms, about 375 micrograms, about 400 micrograms, about 450 micrograms, about 475 micrograms, or about 500 micrograms of the antimicrobial compound is released in vitro per day after the initial 7 day period of release.

In another embodiment, a therapeutically effective amount is achieved when between about 5 micrograms and about 300 micrograms of the antimicrobial compound is released in vivo per gram of vaginal fluid each day for 24 days after an initial 3 day period of use. In another embodiment, a therapeutically effective amount is achieved when between about 10 micrograms and about 100 micrograms of the antimicrobial compound is released in vivo per gram of vaginal fluid each day for 24 days after an initial 3 day period of use. In another embodiment, a therapeutically effective amount is achieved when between about 20 micrograms and about 80 micrograms of the antimicrobial compound is released in vivo per gram of vaginal fluid each day for 24 days after an initial 3 day period of use. In yet another embodiment, a therapeutically effective amount is achieved when about 5 micrograms, about 10 micrograms, about 25 micrograms, about 50 micrograms, about 75 micrograms, about 100 micrograms, about 125 micrograms, about 150 micrograms, about 175 micrograms, about 200 micrograms, about 225 micrograms, about 250 micrograms, about 275 micrograms, about 300 micrograms, about 350 micrograms, about 400 micrograms, about 450 micrograms, about 500 micrograms, or about 600 micrograms of the antimicrobial compound is released in vivo per gram of vaginal fluid each day for 24 days after an initial 3 day period of use.

Values and ranges included and/or intermediate within the ranges set forth herein are also intended to be within the scope of the present disclosure. Ranges having values recited herein as an upper or lower limit are also intended to be within the scope of the present disclosure.

Those of skill in the prevention and/or treatment of HIV could determine the appropriate therapeutically effective amount or prophylactically effective amount from the data presented here. The exact dosage may depend on the particular antimicrobial compound used.

The term "subject" means female humans who use the rings. Administration of the rings of the present invention to a subject can be carried out using known procedures, at dosages and for periods of time effective to treat or prevent HIV.

As used herein, the term "vagina" or "vaginal" refers to the passage leading from the opening of the vulva to the cervix of the uterus in female humans. As used herein, the term "intravaginal administering" refers to the administration of a ring of the invention to the vagina of a female human.

The rings of the present invention may be administered into the vagina of a subject prior to sexual intercourse, e.g., 1, 2, 3, 4, 5 or 6 weeks, prior to sexual intercourse. In some embodiments, the rings of the invention may be administered into the vagina of a subject after sexual intercourse, e.g., 1, 2, 3, 4, 5, 6, 7, 8, 9, 10, 11, 12, 13, 14 or 15 days after sexual intercourse.

The term sexual intercourse means vaginal sex.

The term "partners" as used herein defines two or more humans, who are sexually active with each other, i.e., who have sexual intercourse with each other.

As used herein, the term "preventing HIV infection" includes the application or administration of an intravaginal ring of the invention to a subject who is at risk of developing HIV, or who has been exposed to but not yet developed HIV, in order to decrease the likelihood that the subject will develop HIV. In one embodiment of the invention, proper use of the intravaginal rings of the invention leads to prevention of HIV infection in about 1%, about 5%, about 10%, about 15%, about 20%, about 25%, about 30%, about 35%, about 40%, about 45%, about 50%, about 55%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, a %, a 93%, about 94%, about 95%, about 96%, about 97%, about 98%, about 99% or about 100% of the subjects who are at risk of developing HIV or who have been exposed to but not yet developed HIV. Values and ranges included and/or intermediate within the ranges set forth herein are also intended to be within the scope of the present disclosure. Ranges having values recited herein as an upper or lower limit are also intended to be within the scope of the present disclosure.

The term "treating" includes the application or administration of an intravaginal ring of the invention to a subject, or application or administration of an intravaginal ring of the invention to a subject who has HIV, with the purpose of curing, healing, alleviating, relieving, altering, remedying, ameliorating, preventing, improving, or affecting HIV. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being. Treatment may be therapeutic or prophylactic. The treatment or amelioration of symptoms can be based on objective or subjective parameters; including the results of a physical examination.

IV. Methods for Preparing Rings of the Invention

Rings of the invention may be manufactured by any method known by those skilled-in-the-art, but preferably by injection molding or extrusion, and more preferably by reaction injection molding of silicone elastomer systems. The term 'injection molding' refers to manufacturing processes for producing parts/devices from either thermoplastic or thermosetting materials using suitably designed injection molds. Examples of thermoplastic materials include polyethylene and PEVA; examples of thermosetting materials include silicone rubbers/elastomers. Without limitation, matrix-type silicone elastomer rings containing dapivirine may be prepared by (i) adding and mixing the dapivirine into one or more components of the silicone system (e.g. base, crosslinking agent, catalyst, excipient, dispersant, etc) (ii) injecting the mix into suitably designed injection molds, and (iii) optionally, applying heat to cause the silicone mix to cure/crosslink forming an elastomer.

The present invention further provides methods of preparing the platinum-catalyzed rings of the invention described above in Section I. These methods generally comprise dispersing dapivirine and an elastomer, e.g., polysiloxane, in an appropriate solvent or dispersing agent, e.g., silicone liquid, and curing the rings with a platinum catalyst, e.g., a platinum-siloxane complex, thereby preparing a platinum-catalyzed ring. Any of the well-known elastomers, e.g., polysiloxanes, described supra may be used to prepare the platinum-catalyzed rings of the invention. In one embodiment, an elastomer, e.g., polysiloxane, for use in the methods of the invention is a dimethylsiloxane, e.g., vinyl-terminated polydimethylsiloxane. In another embodiment, an elastomer, e.g., polysiloxane, for use in the methods of the invention is a diorganopopolysiloxane, e.g., dimethylpolysiloxane. In another embodiment, the elastomer, e.g., polysiloxane, for use in the methods of the invention is MED-8470. In certain embodiments, the methods further comprise use of a cross-linker, e.g., hydride functional polydimethylsiloxane or dimethylmethylhydrogen polysiloxane cross-link.

In one embodiment, the method further comprises catalyzing the rings in a ring mould. The mould can then be opened, following which the intravaginal ring is removed and trimmed. Ring moulds, are preferably coated with, for example, Teflon™ or an electrolytically applied metalised coating. Ring moulds may be constructed of hardened carbon steel, stainless steel, aluminum, or any other material deemed to be appropriate. It will be appreciated that the mould dimensions and design impart the physical shape of the intravaginal drug delivery device, for example, a partial or complete ring, or any other desired shape. Preferably, the device has a partial or complete toroidal shape, more preferably a partial or complete torus shape, or a substantially cylindrical shape. By toroid is meant a ring-like body generated by rotating any closed loop (including an ellipse, a circle or any irregular curve) about a fixed line external to that loop. The toroid shape may be a complete or partial toroid. By torus is meant a ring-like body generated by rotating a circle about a fixed line external to the circle. The torus shape may be a complete or partial ring-like shape. The geometric characteristics of the mould and intravaginal rings can be varied as required by the use.

Alternatively, the intravaginal ring device, or components thereof, may be prepared by extrusional processes, e.g., co-extrusion or blend extrusion, well known to those skilled in the art (see, e.g., U.S. Pat. No. 5,059,363, the entire contents of which are incorporated herein by reference).

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

The production of solid state silicone (cured or cross-linked silicone) can be achieved in a number of ways, including addition (or hydrosilation) cure and condensation cure. The catalyst selected depends on the targeted cross-linking reaction. Previous dapivirine matrix rings were based on a tin-catalyzed condensation reaction for cross-linking, resulting in the formation of alcohol by-products. This cross-linking reaction, or curing phase, continues beyond manufacture of the ring product. As the cross-linking reaction continues, the generation of alcohol by-product (in this case, propanol) also continues. This generation of alcohol by-product contributes to an increased rate of migration of dapivirine from within the matrix of the ring to the surface, resulting in crystalline deposits of dapivirine on the surface of the rings. This was noted on inspection of rings on stability at both long term (25° C./60% & 30° 65% RH) and accelerated (40°/75% RH) storage conditions. Accordingly, the instant invention provides improved intravaginal rings.

Example 1

Dapivirine Matrix Vaginal Ring

Stability issues were addressed by the development of the instant dapivirine ring. Specifically, a silicone curing reaction used a different catalyst for the cross-linking reaction. The instant invention provides rings with a dispersion of 25 mg dapivirine in a silicone elastomer matrix (matrix ring); however, platinum (in the form of a platinum-siloxane complex) is used as the catalyst for the silicone crosslinking reaction. This process is readily applied in scale-up production and does not involve a propanol by-product produced during curing.

The dapivirine matrix vaginal ring is an off-white flexible ring containing 25 mg of drug substance dispersed in a silicone matrix (see Table 1 for composition of the ring). The dimensions of the ring are 56 mm and 7.7 mm outer diameter and cross-sectional diameter, respectively. The vaginal ring is designed to provide sustained release.

TABLE 1

Composition of an 25 mg Dapivirine Intravaginal Ring

| Components | Function | Amount per Ring |
|---|---|---|
| Dapivirine (4-[[4-[(2,4,6-trimethylphenyl)amino]-2-pyrimidinyl]amino]benzonitrile) | Active pharmaceutical ingredient | 25 mg |
| Silicone liquid (NuSil MED360) | Dispersing agent | 175 mg |
| Silicone elastomer Part A (NuSil MED4870 Part A)[1] | | |
| Vinyl-terminated polydimethylsiloxane (linear) polymers | Polymer | 3900 mg |
| Platinum-siloxane complex | Catalyst for crosslinking reaction | |
| ~30% amorphous (non-crystalline) reinforcing silica | Filler | |
| Silicone elastomer Part B (NuSil MED4870 Part B) | | |
| Vinyl-terminated polydimethylsiloxane (linear) polymers | Polymer | 3900 mg |
| Hydride functional polydimethysiloxane polymer | Cross-linker | |
| ~30% amorphous (non crystalline) reinforcing silica | Filler | |

[1]Part A&B refer to a two-part translucent silicone system used with injection molding equipment.

Example 2

Release Characteristics of Dapivirine from Vaginal Rings Consisting of Ethylene Vinyl Acetate, Silicone or Polyurethane Polymers

To date, most microbicide candidates in clinical evaluation have been formulated as single-use, semi-solid gels designed to be administered to the vagina immediately before each act of intercourse (Garg et al., *Antivir. Chem. Chemother.*, 2009; 19(4):143-450.) However, a clear rationale exists for the development of controlled-release microbicide formulations, potentially offering 1) long-term continuous protection against sexually-transmitted HIV, 2) increased acceptability, and 3) improved user adherence which should translate into greater product effectiveness.

Dapivirine possesses specific hydrophilic/lipophilic characteristics, as evidenced by its relatively large and positive log P value, which are likely to influence its release characteristics from polymeric ring devices (Table 2). Accordingly, this example compares the in vitro drug release characteristics of dapivirine from vaginal rings fabricated from various polymers: silicone, EVA, and polyurethane (PU).

TABLE 2

| Dapivirine | |
|---|---|
| Log P (n-octanol and buffer) | 5.27 at pH 9.0 |
| Solubility Profile (Low Solubility) | 0.1N HCl = 0.28 mg/mL |
| | Water = >0.001 mg/mL |
| | PEG 400 = 47.4 mg/g |
| | Propylene Glycol = 2.69 mg/g |
| pKa | 5.8 |

Matrix-type vaginal rings were manufactured by injection molding of either silicone, EVA or PU polymers containing dapivirine (Table 3). All polymers were compounded in a matrix style configuration with drug substance evenly distributed throughout the matrix of the polymer. In vitro release testing was performed under sink conditions with HPLC/UV quantification of microbicide concentrations.

TABLE 3

| Ring Description | |
|---|---|
| Polymer | Dapivirine |
| Silicone | Opaque/Dispersed |
| | 0.31% wt/wt, 25 mg |
| | Injection molded 180° C. |
| | 56 mm OD, 7.7 mm CSD |
| | (1:1 isopropanol:water) |
| EVA | Opaque/Dispersed |
| | 1.3% wt/wt, 23 mg |
| | melt extruded |
| | injection molded 120-150° C. |
| | 54 mm OD, 4 mm CSD |
| | (1:1 isopropanol: = water) |
| Polyurethane | Transparent |
| | 0.5% wt/wt, 15 mg |
| | melt extruded at 180° C. |
| | 58.4 mm OD, 4.4 mm CSD |
| | (1:3 isopropanol:buffer) |

Typical root-time kinetics were observed in vitro for dapivirine in all three polymers under sink conditions. A large initial burst was observed over Days 1-3, followed by a moderate decline in daily release rate through Day 30. As demonstrated in FIG. 1, the percent release of dapivirine is greatest for EVA (95%) and PU (79%) and least from silicone (44%). The release of dapivirine from silicone and PU exhibit traditional root-time kinetics. Dapivirine release from EVA follows root-time kinetics through approximately 68% release of drug load. However, after 30 days, almost 100% of the total drug load has been released from EVA, so that in the later stages of release when drug is almost exhausted, first order kinetics are obeyed.

In an attempt to negate the impact of ring dimensions on in vitro release rates, the cumulative release data were evaluated based on flux of the compounds from each of the polymers. The data were then normalized with respect to surface area with a ring dimension of 54 mm OD and 4 mm CSD and an overall surface area of 2052 $mm^2$. Normalization of dapivirine flux from each polymer assumes a linear relationship with respect to drug load between 0.3% and 1.3%.

Figure 2:
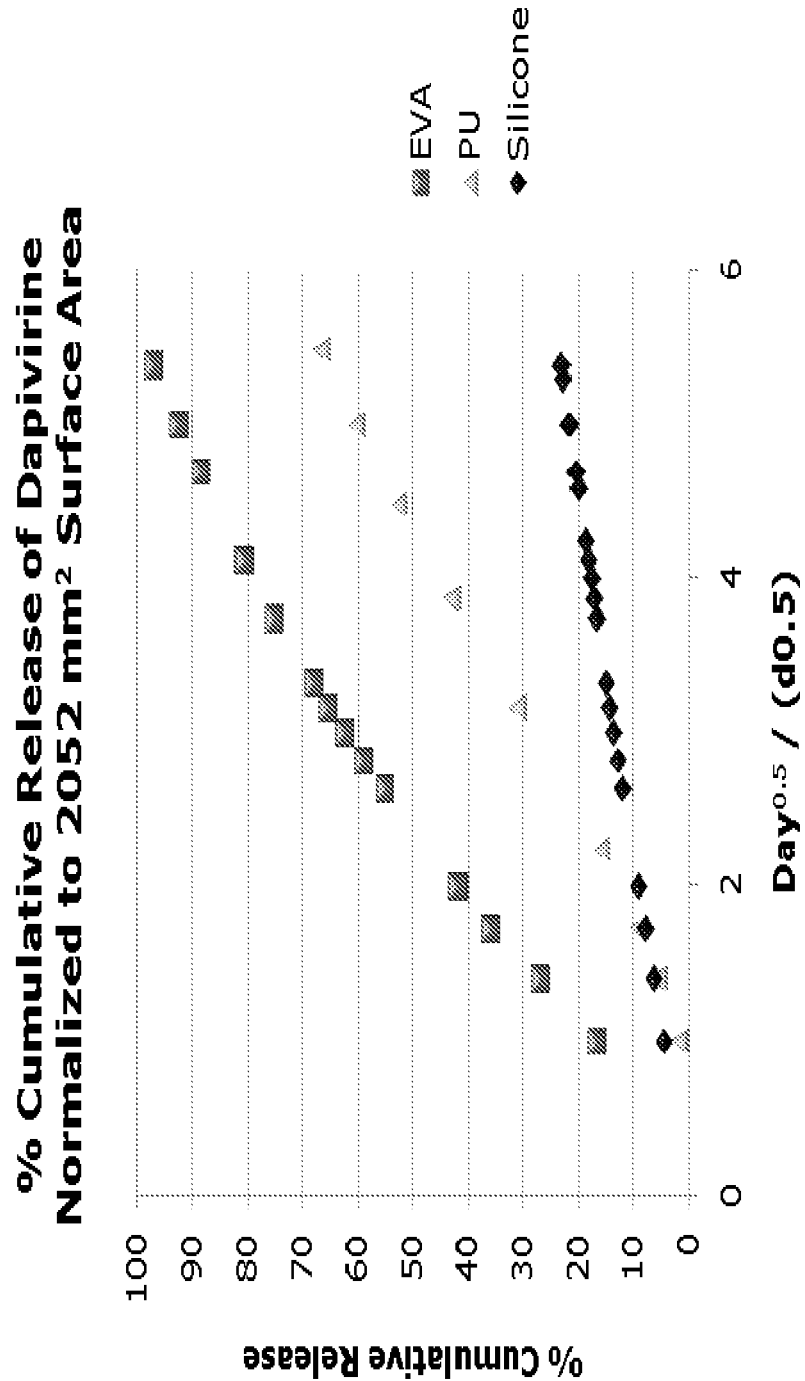
FIG. 2 depicts the percent cumulative release of dapivirine normalized to 2052 mm$^2$ surface area from various polymers, such as silicone, EVA and polyurethane (PU).

FIG. 2 demonstrates the flux of dapivirine in vitro from each polymer type. Since the silicone ring has a larger ring dimension than the EVA and PU rings, and was normalized against the smaller ring dimensions, the greatest impact is to the silicone ring (FIG. 2). However, rank order of release of dapivirine from the various polymers is unchanged. In general, drug release was observed to be dependent on drug loading and type of polymer.

The release of microbicides from polymer matrices is highly dependent on the physical and chemical characteristics of both the drug substance and the polymer. Dapivirine readily diffuses through silicone, EVA and PU polymers. The very different solubility characteristics of the microbicide compounds in the various polymer systems has a significant impact on drug release. Each of the polymer systems offers a viable formulation option for development of anti-HIV microbicide vaginal ring products.

In general, release rates of dapivirine can be altered from matrix configuration formulations based on polymer type, polymer grade, use of excipients and fillers, as well as drug load. However, release of dapivirine from EVA is relatively independent of EVA type (melt index or percent vinyl acetate).

The intravaginal rings of the invention, which contain a single antiretroviral compound, have been successfully formulated to provide sustained release, thereby demonstrating that vaginal rings are a viable dosage form for the development of antimicrobial compounds.

Example 3

Comparative Study of Dissolution Profiles of Microbicide Ring Products Prepared from Different Silicone Elastomer Sources Vaginal rings are sustained release delivery formulations of the drug substance in polymer bases. Different vendors produce silicone elastomers of different formulations with varying crosslinker and filler contents. This example compares the in vitro release characteristics of the matrix-type microbicide rings made from silicone materials marketed by four vendors.

The drug product device was prepared by blending the silicone elastomer base with Dapivirine, a potent antiviral compound against HIV-1. Each ring contained 25 mg of the drug substance dispersed in a platinum cured silicone matrix (FIG. 3). Dissolution testing was performed on silicone matrix rings in 1:1 Isopropyl alcohol (IPA):Water dissolution medium. Each ring was placed in a borosilicate bottle with 100 mL of the de-aerated dissolution medium and then incubated in orbital shakers at 37° C. and 60 rpm until sampling. The vaginal rings were changed into fresh dissolution medium daily. For the vaginal ring product the sampling of the medium was carried out daily for 28 days. The 24 hours sampling provides information of the initial burst period. Quantification of the drug in the dissolution samples was achieved by reversed phase HPLC using UV detection at 287 nm (FIG. 4).

The in vitro release data showed that the dissolution profiles of the silicone rings were not impacted by the different chemistries of the four variants of the product (FIGS. 5 and 6). The Day 1 release as well as the cumulative drug releases at 7, 14, 21 and 28 days of dissolution were similar with % RSD range of 2.0% to 8.0%. Data from the set of 3 replicates of each variant showed that the results were reproducible suggesting the dissolution testing procedure can also provide a reliable means to control the quality of these products.

The results of this example demonstrate that the choice of the type of proprietary silicone base may not be critical for gauging the performance of the dapivirine silicone matrix vaginal ring in vivo. Dapivirine released from the rings after long-term storage was not materially different from that at release (FIGS. 7 and 8), nor were related compounds observed in the chromatograms, suggesting that dapivirine binding with the polymeric matrix is unlikely and the formulations are stable.

Example 4

Comparative Studies of Dapivirine Levels in Cervical Fluids Resulting from Clinical Use of Tin Catalyzed and Platinum Catalyzed Silicone Rings Containing Dapivirine In Vivo A steady release of drug substance from a vaginal ring is preferred and likely more efficient in delivering drug substance for the prevention if HIV infection than an initial "burst" in the first 24 hours, followed by a declining release rate. This example compares dapivirine levels in cervical fluids resulting from clinical use of tin catalyzed and platinum catalyzed silicone matrix rings containing dapivirine in vivo.

In one study eight women used tin catalyzed silicone rings containing 25 mg of dapivirine for 28 days. In another study eight women used platinum catalyzed silicone rings containing 25 mg of dapivirine for 28 days. In both studies samples of cervical fluids were taken five times during the first 24 hours after insertion, daily for the remainder of the first week, and weekly thereafter until removal of the ring. Samples of cervical fluid were analyzed to determine the level of dapivirine present in the cervical fluid on the date of each sample. The results are shown in FIG. 9. FIG. 9 shows the mean of the values observed in the eight women participating in the study.

As indicated in FIG. 9, cervical fluid concentrations of dapivirine remained more constant over time for the platinum-catalyzed ring than for the tin-catalyzed ring. Data for the tin catalyzed ring show an initial "burst" of drug substance present in the cervical fluid, followed by declining levels until removal of the ring. In contrast, data for the platinum catalyzed ring show no initial "burst," and the level of drug substance showed relatively little decline after reaching the level observed on the third day after insertion. The platinum catalyzed ring therefore achieved in vivo a steady release rate that was not observed in the tin catalyzed ring, and that is more typically associated with reservoir rings.

EQUIVALENTS

Those skilled in the art will recognize, or be able to ascertain using no more that routine experimentation, many equivalents to the specific embodiments of the invention described herein. Such equivalents are intended to be encompassed by the following claims.

We claim:

1. A platinum-catalyzed silicone intravaginal matrix-type ring comprising a non-nucleoside reverse transcriptase inhibitor (NNRTI), wherein between about 1 mg and about 3 mg of said NNRTI is released in vitro from said ring during an initial 24 hour period of release, wherein between about 100 and about 500 micrograms of said NNRTI is released in vitro each day for 21 days after an initial 7 day period of release, and wherein the NNTRI is homogenously distributed throughout the ring.

2. The platinum-catalyzed silicone intravaginal ring of claim 1, wherein use of the ring in vivo results in a steady level of between about 5 micrograms and about 300 micrograms of the NNRTI per gram of vaginal fluid for 24 days after an initial 3 day period of use.

3. The platinum-catalyzed silicone intravaginal ring of claim 1, wherein the NNRTI is present in the ring in a therapeutically effective amount.

4. The platinum-catalyzed silicone intravaginal ring of claim 1, wherein the NNRTI is present in the ring in a prophylactically effective amount.

5. The platinum-catalyzed silicone intravaginal ring of claim 1, wherein about 10 to about 30 mg of the NNRTI is present in the ring.

6. The platinum-catalyzed silicone intravaginal ring of claim 1, wherein about 20 to about 30 mg of the NNRTI is present in the ring.

7. The platinum-catalyzed silicone intravaginal ring of claim 1, wherein about 10 to about 800 mg of the NNRTI is present in the ring.

8. The platinum-catalyzed silicone intravaginal ring of claim 1, wherein about 25 mg of the NNRTI is present in the ring.

9. The platinum-catalyzed silicone intravaginal ring of claim 1, wherein NNRTI release rates are stable following 3 months of storage.

10. The platinum-catalyzed silicone intravaginal ring of claim 1, wherein NNRTI release rates are stable following 6 months of storage.

11. The platinum-catalyzed silicone intravaginal ring of claim 1, wherein NNRTI release rates are stable following 12 months of storage.

12. The platinum-catalyzed silicone intravaginal ring of claim 1, wherein NNRTI release rates are stable following 36 months of storage.

13. The platinum-catalyzed silicone intravaginal ring of claim 1, wherein no crystalline deposits of NNRTI are formed on the surface of the ring.

14. The platinum-catalyzed silicone intravaginal ring of claim 1, wherein the ring does not contain alcohol by-products.

15. The platinum-catalyzed silicone intravaginal ring of claim 14, wherein the ring does not contain propanol by-products.

16. The platinum-catalyzed silicone intravaginal ring of claim 1, wherein the NNRTI is a substituted di-amino-pyrimidine derivative.

17. The platinum-catalyzed silicone intravaginal ring of claim 16, wherein the di-amino-pyrimidine derivative is dapivirine.

18. The platinum-catalyzed silicone intravaginal ring of claim 1, wherein the intravaginal ring has an outer diameter of 56 mm.

19. The platinum-catalyzed silicone intravaginal ring of claim 1, wherein the intravaginal ring has a cross-sectional diameter of 7.6 mm.

20. A platinum-catalyzed silicone intravaginal matrix-type ring comprising a non-nucleoside reverse transcriptase inhibitor (NNRTI), wherein between about 5 micrograms and about 300 micrograms of said NNRTI are released in vivo from said ring per gram of vaginal fluid for 24 days after an initial 3 day period of use, and wherein the NNTRI is homogenously distributed throughout the ring.

21. The platinum-catalyzed silicone intravaginal ring of claim 20, wherein the NNRTI is present in the ring in a therapeutically effective amount.

22. The platinum-catalyzed silicone intravaginal ring of claim 20, wherein the NNRTI is present in the ring in a prophylactically effective amount.

23. The platinum-catalyzed silicone intravaginal ring of claim 20, wherein about 10 to about 30 mg of the NNRTI is present in the ring.

24. The platinum-catalyzed silicone intravaginal ring of claim 20, wherein about 20 to about 30 mg of the NNRTI is present in the ring.

25. The platinum-catalyzed silicone intravaginal ring of claim 20, wherein about 10 to about 800 mg of the NNRTI is present in the ring.

26. The platinum-catalyzed silicone intravaginal ring of claim 20, wherein about 25 mg of the NNRTI is present in the ring.

27. The platinum-catalyzed silicone intravaginal ring of claim 20, wherein NNRTI release rates are stable following 3 months of storage.

28. The platinum-catalyzed silicone intravaginal ring of claim 20, wherein NNRTI release rates are stable following 6 months of storage.

29. The platinum-catalyzed silicone intravaginal ring of claim 20, wherein NNRTI release rates are stable following 12 months of storage.

30. The platinum-catalyzed silicone intravaginal ring of claim 20, wherein NNRTI release rates are stable following 36 months of storage.

31. The platinum-catalyzed silicone intravaginal ring of claim 20, wherein no crystalline deposits of NNRTI are formed on the surface of the ring.

32. The platinum-catalyzed silicone intravaginal ring of claim 20, wherein the ring does not comprise alcohol by-products.

33. The platinum-catalyzed silicone intravaginal ring of claim 32, wherein the ring does not contain propanol by-products.

34. The platinum-catalyzed silicone intravaginal ring of claim 20, wherein the intravaginal ring has an outer diameter of 56 mm.

35. The platinum-catalyzed silicone intravaginal ring of claim 20, wherein the intravaginal ring has a cross-sectional diameter of 7.6 mm.

36. The platinum-catalyzed silicone intravaginal ring of claim 20, wherein between about 10 micrograms and about 100 micrograms of said NNRTI are released in vivo from said ring per gram of vaginal fluid for 24 days after an initial 3 day period of use.

37. The platinum-catalyzed silicone intravaginal ring of claim 36, wherein between about 20 micrograms and about 80 micrograms of said NNRTI are released in vivo from said ring per gram of vaginal fluid for 24 days after an initial 3 day period of use.

38. The platinum-catalyzed silicone intravaginal ring of claim 20, wherein the NNRTI is a substituted di-amino-pyrimidine derivative.

39. The platinum-catalyzed silicone intravaginal ring of claim 38, wherein the di-amino-pyrimidine derivative is dapivirine.

40. A method of blocking DNA polymerization by an HIV reverse transcriptase enzyme in a female human, comprising the step of inserting the intravaginal ring of claim 1 or claim 20 into the vagina of the female human.

41. A method of decreasing the likelihood that a female human will develop HIV, comprising the step of inserting the intravaginal ring of claim 1 or claim 20 into the vagina of the female human compared to a female human who does not have the intravaginal ring.

42. A method of treating HIV infection in a female human, comprising the step of inserting the intravaginal ring of claim 1 or claim 20 into the vagina of the female human.

* * * * *